United States Patent
Williams et al.

(10) Patent No.: US 10,202,327 B2
(45) Date of Patent: Feb. 12, 2019

(54) HIGHLY ROBUST EFFICIENT CATALYST FOR SELECTIVE DEHYDROGENATION OF NEAT GLYCEROL TO LACTIC ACID

(71) Applicant: UNIVERSITY OF SOUTHERN CALIFORNIA, Los Angeles, CA (US)

(72) Inventors: Travis J. Williams, Los Angeles, CA (US); Zhiyao Lu, Duarte, CA (US); Ivan Demianets, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 15/422,728

(22) Filed: Feb. 2, 2017

(65) Prior Publication Data
US 2017/0217870 A1    Aug. 3, 2017

Related U.S. Application Data

(60) Provisional application No. 62/290,199, filed on Feb. 2, 2016.

(51) Int. Cl.
| | | |
|---|---|---|
| *C07C 51/295* | (2006.01) | |
| *C01B 3/32* | (2006.01) | |
| (Continued) | | |

(52) U.S. Cl.
CPC ......... *C07C 51/295* (2013.01); *B01J 31/2295* (2013.01); *C01B 3/326* (2013.01);
(Continued)

(58) Field of Classification Search
CPC ....... C07C 59/08; C07C 51/16; C07C 51/295; B01J 2231/763; B01J 2531/827;
(Continued)

(56) References Cited

U.S. PATENT DOCUMENTS

| | | | | |
|---|---|---|---|---|
| 6,605,200 B1* | 8/2003 | Mao | ........................ | C07F 9/005 204/403.04 |
| 6,909,009 B2* | 6/2005 | Koridze | ............... | B01J 31/1895 420/900 |
| 2016/0023200 A1* | 1/2016 | Goussev | ................. | C07B 31/00 546/12 |

OTHER PUBLICATIONS

Chiswell et al. "Bidentate Chelate Compounds. III.1 Metal Complexes of Some Pyridyl-Imidazole Derivatives " Inorganic Chemistry, Jan. 1964, vol. 3, No. 1, p. 110-114 (Year: 1964).*

\* cited by examiner

*Primary Examiner* — Amber R Orlando
*Assistant Examiner* — Syed I Iqbal
(74) *Attorney, Agent, or Firm* — Brooks Kushman P.C.

(57) ABSTRACT

A catalyst system includes a complex having formula I which advantageously has a sterically protecting N-heterocyclic carbene (NHC) carbene-pyridine ligand to handle harsh reactions conditions than many prior art catalysts:

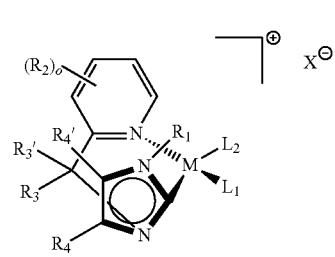

wherein M is a transition metal; o is 0, 1, 2, 3, or 4; $R_1$ is a $C_{1-6}$ alkyl, a $C_{6-18}$ aryl, or an optionally substituted $C_{5-18}$ heteroaryl. In a refinement, $R_1$ is methyl, ethyl, butyl, n-propyl, isopropyl, n-butyl, sec-butyl, or t-butyl; $R_2$, $R_3$, $R_3'$ (Continued)

are independently an optionally substituted $C_{1-6}$ alkyl, halo (e.g., Cl, F, Br, etc), $NO_2$, an optionally substituted $C_{6-18}$ aryl, or an optionally substituted $C_{5-18}$ heteroaryl; $R_4$, $R_4'$ are independently an optionally substituted $C_{1-6}$ alkyl, halo, $NO_2$, an optionally substituted $C_{6-18}$ aryl, or an optionally substituted $C_{5-18}$ heteroaryl; and $X^-$ is a negatively charge counter ion and $L_1$, $L_2$ are each independently a neutral ligand.

19 Claims, 23 Drawing Sheets

(51) Int. Cl.
    *C01D 7/14*       (2006.01)
    *C07F 15/00*     (2006.01)
    *B01J 31/22*      (2006.01)
    *C07C 51/16*      (2006.01)

(52) U.S. Cl.
    CPC ................ *C01D 7/14* (2013.01); *C07C 51/16* (2013.01); *C07F 15/0033* (2013.01); *B01J 2231/763* (2013.01); *B01J 2531/827* (2013.01); *C01B 2203/0227* (2013.01); *C01B 2203/1064* (2013.01); *C01B 2203/1223* (2013.01)

(58) Field of Classification Search
    CPC .......... B01J 31/2295; C01B 2203/0227; C01B 2203/1064; C01B 2203/1223; C01B 3/326; C01D 7/14; C07F 15/0033
    See application file for complete search history.

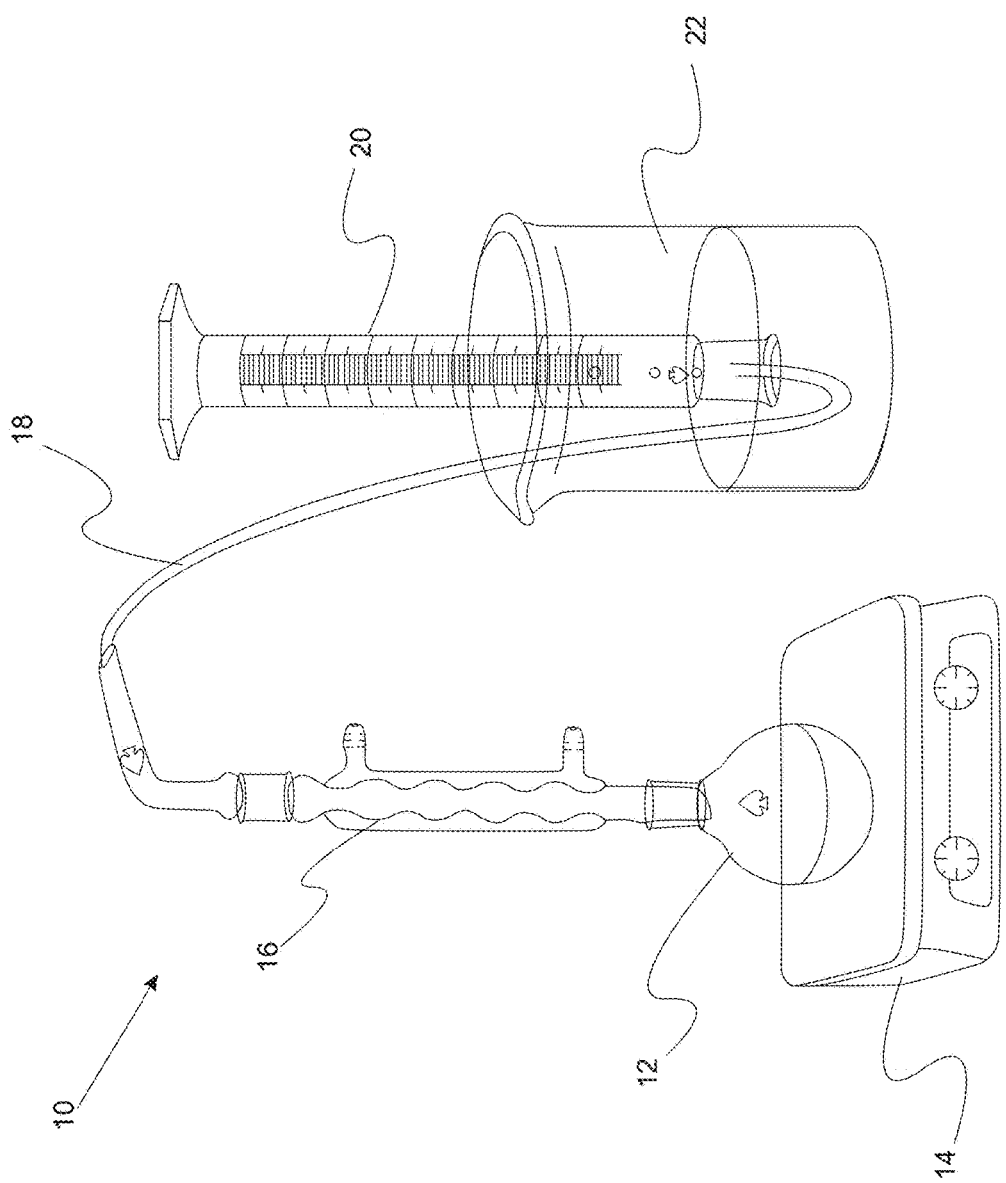

HIGHLY ROBUST EFFICIENT CATALYST FOR SELECTIVE DEHYDROGENATION OF NEAT GLYCEROL TO LACTIC ACID

CROSS-REFERENCE TO RELATED APPLICATIONS

This application claims the benefit of U.S. provisional application Ser. No. 62/290,199 filed Feb. 2, 2016, the disclosure of which is hereby incorporated in its entirety by reference herein.

STATEMENT REGARDING FEDERALLY SPONSORED RESEARCH OR DEVELOPMENT

The invention was made with Government support under Contract No. CHE-1054910 and Contract No. DBI-0821671, CHE-0840366 awarded by the National Science Foundation; and under Contract No. 1 S10 RR25432 awarded by the National Institute of Health, National Center for Research Resources. The Government has certain rights to the invention.

TECHNICAL FIELD

In at least one aspect, the present invention is related to catalyst systems for oxidizing polyols.

BACKGROUND

Glycerol is a byproduct of biodiesel production and of other fine chemical syntheses, such as those of perfumes, fragrances, and pharmaceuticals.[1] Currently the biodiesel industry in the United States produces 2.0 billion gallons of glycerol each year,[2] with an increase projected in the future.[3] Because glycerol constitutes about 10% of the weight of crude biodiesel, the utilization of this "waste" is an opportunity for new technology.[4] Significant effort has been invested in catalytic conversion of glycerol to value-added products.[5] Selective dehydrogenation of glycerol to lactic acid is particularly appealing, because lactic acid is both a valuable feedstock for organic synthesis and a precursor for poly(lactic acid) (PLA), a biodegradable polymer. The market demand of PLA is estimated at 150,000 metric tons by 2017 and 400,000 metric tons by 2022.[6] Moreover, when such conversions are conducted by acceptorless dehydrogenation, the byproduct $H_2$ is a readily separable, energy carrier that has value as such. In these regards, homogeneous conversion of glycerol to lactic acid has shown promising reactivity and good selectivity.[7]

Accordingly, there is a need for efficient processes for efficiently converting glycerol to lactic acid, and in particular, poly(lactic acid),

SUMMARY

In an embodiment, a dehydrogenation catalyst system is provided. The catalyst system includes a complex having formula I which advantageously has a chelating N-heterocyclic carbene (NHC) carbene-pyridine ligand to impart stability under reaction conditions that degrade many prior art catalysts:

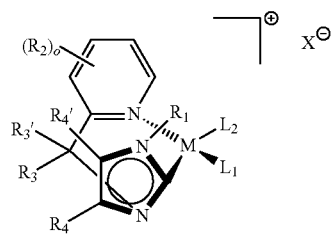

wherein:
M is a transition metal;
o is 0, 1, 2, 3, or 4;
$R_1$ is a $C_{1-6}$ alkyl, a $C_{6-18}$ aryl, or an optionally substituted $C_{5-18}$ heteroaryl. In a refinement, $R_1$ is mesityl, methyl, ethyl, butyl, n-propyl, isopropyl, n-butyl, sec-butyl, or t-butyl;
$R_2$ are independently an optionally substituted $C_{1-6}$ alkyl, halo (e.g., Cl, F, Br, etc), $NO_2$, an optionally substituted $C_{6-18}$ aryl, or an optionally substituted $C_{5-18}$ heteroaryl;
$R_3$, $R_3'$ are independently hydrogen, an optionally substituted $C_{1-6}$ alkyl, halo (e.g., Cl, F, Br, etc), $NO_2$, an optionally substituted $C_{6-18}$ aryl, or an optionally substituted $C_{5-18}$ heteroaryl;
$R_4$, $R_4'$ are independently hydrogen, an optionally substituted $C_{1-6}$ alkyl, halo (e.g., Cl, F, Br, etc), $NO_2$, an optionally substituted $C_{6-18}$ aryl, an optionally substituted $C_{5-18}$ heteroaryl, or an annulated aromatic ring;
$X^-$ is a negatively charge counter ion such as halide or trifluoromethanesulfonate (OTf); and
$L_1$, $L_2$ are each independently a neutral ligand.

In another embodiment, a method for dehydrogenation of an alcohol is provided. The method includes a step contacting an alcohol (e.g., methanol) having formula $R_6OH$ with a catalyst system that includes an organometallic complex having formula I set forth above to form an oxidized compound or to liberate hydrogen,

BRIEF DESCRIPTION OF THE DRAWINGS

FIGS. 3A and 3B. Apparatus set up for dehydrogenation reactions (A) and typical kinetic profile (B).

DETAILED DESCRIPTION

Figure 1A:
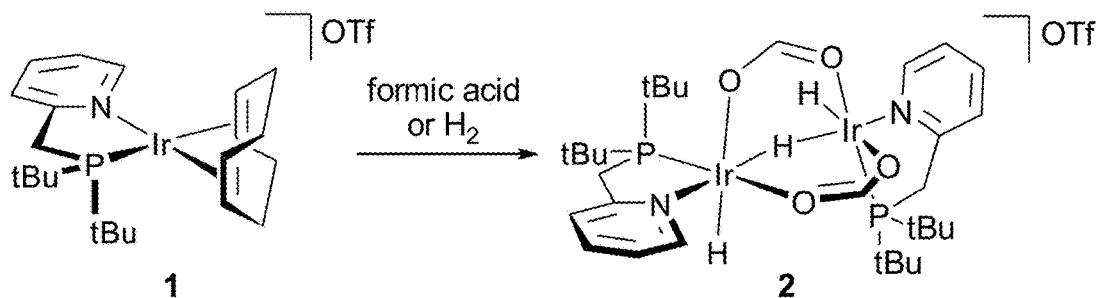
FIGS. 1A, 1B, and 1C. Scheme 1. (A) Formic acid dehydrogenation system 1/2, (B) Syntheses, and (C) molecular structures[8] of novel iridium complexes. Ellipsoids drawn at the 50% probability level.
Figure 1B:
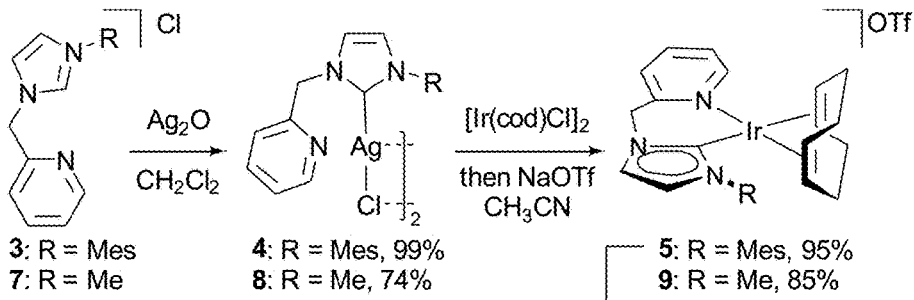
Figure 1C:
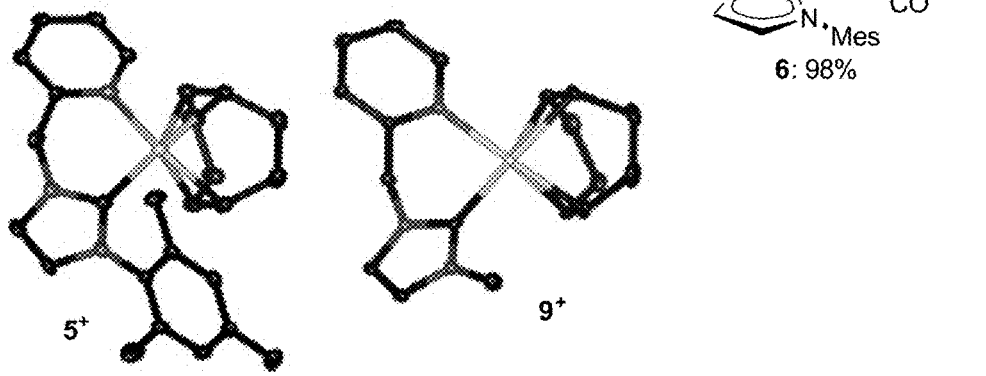
Figure 2A:
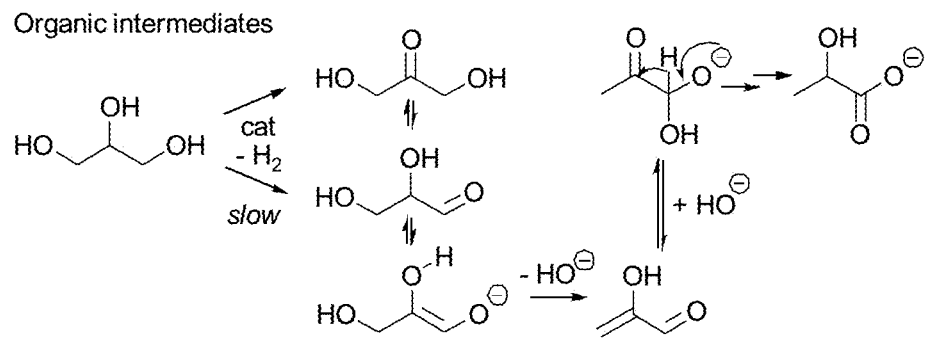
FIGS. 2A and 2B. A mechanistic model for catalytic glycerol dehydrogenation with 9 (Scheme 2). (A) Organic Intermediates and (B) Catalytic Cycle.
Figure 2B:
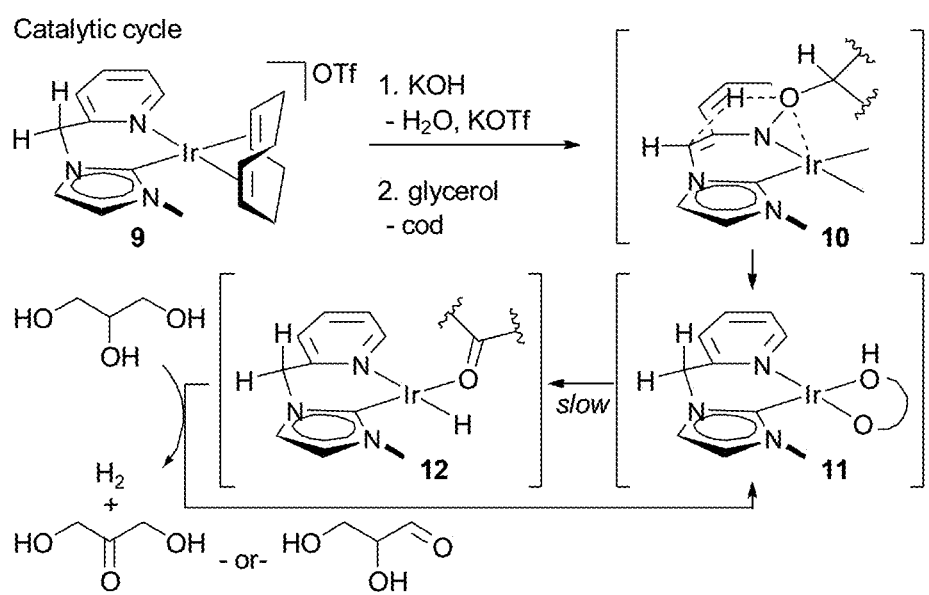

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. R$_i$ where i is an integer) include hydrogen, alkyl, lower alkyl, C$_{1-6}$ alkyl, C$_{6-10}$ aryl, or C$_{6-10}$ heteroaryl; single letters (e.g., "n" or "o") are 0, 1, 2, 3, 4, or 5; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The term "alkyl" refers to C$_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In the formulae set forth herein, alkyl can be any of these moieties.

Throughout this application, where publications are referenced, the disclosures of these publications in their entireties are hereby incorporated by reference into this application to more fully describe the state of the art to which this invention pertains.

Abbreviations:
"me" is methyl.
"mes" is mesityl:

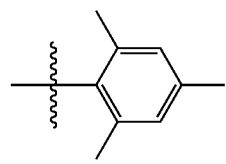 [SMILES: *c1c(C)cc(C)cc1C]

where the wavy line indicates the attached position of the mes group.

"OTf" is trifluoromethanesulfonate.

In an embodiment, a dehydrogenation catalyst system is provided. The catalyst system includes a complex having formula I which advantageously has a sterically protecting NHC carbene-pyridine ligand to handle harsh reactions conditions than many prior art catalysts:

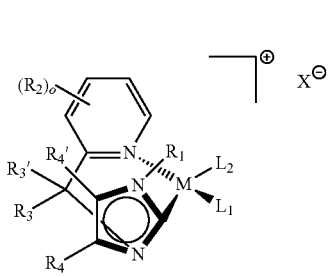

wherein:

M is a transition metal;

o is 0, 1, 2, 3, or 4;

$R_1$ is a $C_{1-6}$ alkyl, a $C_{6-18}$ aryl, or an optionally substituted $C_{5-18}$ heteroaryl. In a refinement, $R_1$ is mesityl, methyl, ethyl, butyl, n-propyl, isopropyl, n-butyl, sec-butyl, or t-butyl;

$R_2$ are independently an optionally substituted $C_{1-6}$ alkyl, halo (e.g., Cl, F, Br, etc), $NO_2$, an optionally substituted $C_{6-18}$ aryl, or an optionally substituted $C_{5-18}$ heteroaryl;

$R_3$, $R_3'$ are independently hydrogen, an optionally substituted $C_{1-6}$ alkyl, halo (e.g., Cl, F, Br, etc), $NO_2$, an optionally substituted $C_{6-18}$ aryl, or an optionally substituted $C_{5-18}$ heteroaryl;

$R_4$, $R_4'$ are independently hydrogen, an optionally substituted $C_{1-6}$ alkyl, halo (e.g., Cl, F, Br, etc), $NO_2$, an optionally substituted $C_{6-18}$ aryl, or an optionally substituted $C_{5-18}$ heteroaryl, or an annulated aromatic ring (i.e., $R_4$ and $R_4'$ are bonded together to form a 5 or 6 member aromatic ring fused to the NHC carbine ring);

$X^-$ is a negatively charge counter ion such as halide or trifluoromethanesulfonate (OTf); and $L_1$, $L_2$ are each independently a neutral ligand. Examples of such ligands include, but are not limited to, carbon monoxide, triphenylphosphine, $CH_3CN$ $C_5H_5N$, $H_2O$, $NH_3$, arene, and combinations thereof, and the like. In a refinement, $L_1$ and $L_2$ are combined together to form a neutral bidentate ligand as illustrated in the following formula II:

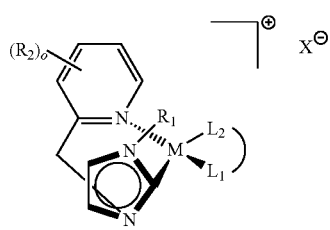

These bidentate ligands can be $C_{5-10}$ bis(alkene) ligands, $C_{5-10}$ bis(alkyne) ligands, $C_{2-10}$ diamine ligands, $C_{2-10}$ diphosphine ligands, $C_{2-10}$ bis(nitrile) ligands, $C_{2-10}$ bis(isonitrile) ligands, and the like. Examples of useful bidentate ligands include, but are not limited to norbornadiene, 1,5-cyclooctadiene, ethylenediamine, 2,2'-bipyridine, and the like.

In a variation, the organometallic complex is described by formula III:

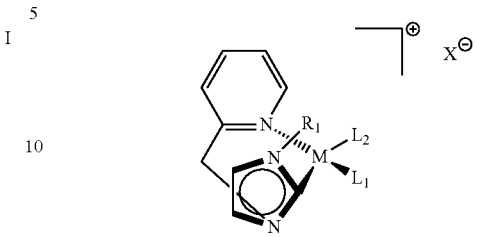

where $R_1$, $L_1$, $L_2$, $X^-$, and M are as set forth herein. Particularly useful organometallic complexes are described by formula IV and V:

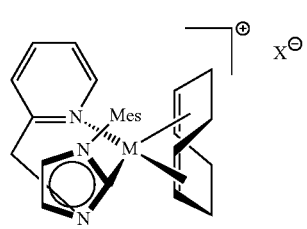

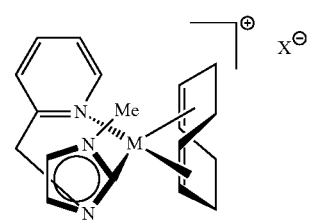

where M and $X^-$ are as set forth herein.

In a refinement, the catalyst system also includes a base as a co-catalyst. In a refinement, the ligands in formulae I-V are optionally substituted with one or more groups at any position with $C_{1-6}$ alkyl, halo, nitro and the like. In another refinement, the ligands in formula I are optionally substituted with one or more groups at any position with methyl, ethyl, butyl, n-propyl, isopropyl, n-butyl, sec-butyl, and/or t-butyl.

In a variation M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium. In a refinement, M is a transition metal selected from the group consisting of ruthenium, rhodium, iridium, and iron. In another refinement, M is iridium.

In another embodiment, a method for dehydrogenation of a polyol is provided. The method includes a step contacting a polyol having formula VI with a catalyst system that includes an organometallic complex having formulae I-V to form an oxidized compound having formula VII:

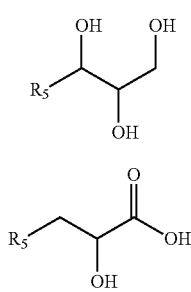

wherein $R_5$ is selected from the group consisting of hydrogen, methyl, ethyl, butyl, n-propyl, isopropyl, n-butyl, sec-butyl, and t-butyl. In a refinement, the catalyst system further comprises a base. In a particularly useful variation, the polyol is glycerol and the oxidized compound having formula III is lactic acid.

In another embodiment, a method for dehydrogenation of an alcohol is provided. The method includes a step contacting an alcohol (e.g., methanol) having formula $R_6OH$ with a catalyst system that includes an organometallic complex having formulae I-V to form an oxidized compound or to liberate hydrogen, wherein $R_6$ is a $C_{1-6}$ alkyl. $R_6$ is selected from the group consisting of methyl, ethyl, butyl, n-propyl, isopropyl, n-butyl, sec-butyl, and t-butyl. In a refinement, the catalyst system further comprises a base. In a particularly useful variation, the polyol is glycerol and the oxidized compound having formula VII is lactic acid.

These examples illustrate the various embodiments of the present invention. Those skilled in the art will recognize many variations that are within the spirit of the present invention and scope of the claims.

Embodiments of the present invention show the most robust and selective catalyst to date for the conversion of glycerol and new insights into its reactive mechanism. The system enables high conversion of neat glycerol, even if isolated crude from biodiesel production, to sodium lactate with >99% selectivity. It is also shown that lactic acid can be easily isolated from our reaction mixture and then converted to rac- and meso-lactides, the precursors for PLA synthesis.

Our entry into glycerol dehydrogenation stemmed from our diiridium catalyst (2) for formic acid dehydrogenation (scheme 1a).[9] In this prior study we found that 2 forms from monomer 1, and that the (pyridyl)methylphosphine ligand plays a vital part in enabling dimer formation and catalyst longevity: other P—N and C—N ligands did not efficiently dimerize or display the reactivity of ½. We further observed that once dimerized, complex 2 had little dehydrogenation reactivity with substrates other than formic acid. On these bases, we designed complexes 5 and 9 (scheme 1bc), which feature bidentate (pyridyl)methylcarbene ligands that apparently inhibit an analogous dimerization and enable more general dehydration reactivity.

TABLE 1

Dehydrogenation of neat glycerol to lactic acid.

| Entry | Catalyst (ppm) | Temp. (° C.) | Time | Base (mol %) | TON | Conversion |
|---|---|---|---|---|---|---|
| 1 | 20 (5) | 145 | 3 d | 25 | 12964 | 25.9% |
| 2[a] | 0.1 (5) | 145 | 8 d | 25 | 1057172 | 10.5% |
| 3 | 20 (5) | 145 | 6 d | 50 | 14901 | 29.8% (22%)[b], |
| 4 | 20 (5) | 145 | 6 d | 100 | 17285 | 34.6% |
| 5 | 100 (5) | 180 | 1 h | 1 | 119 | 1.2% |
| 6 | 100 (5) | 180 | 1.5 h | 10 | 1162 | 11.6% |
| 7 | 20 (5) | 180 | 10 h | 10 | 5215 | 10.4% |
| 8 | 20 (5) | 180 | 15 h | 25 | 13113 | 26.2% |
| 9 | 20 (5) | 180 | 15 h | 50 | 15894 | 31.9% |
| 10[d] | 200 (5) | 145 | 5 d | 50 | 1909 | 38.2% |
| 11[d] | 200 (5) | 145 | 5 d | 100 | 3445 | 68.9% |
| 12 | 20 (6) | 145 | 6 d | 50 | 7490 | 15.0% |
| 13 | 20 (6) | 145 | 6 d | 100 | 10785 | 21.6% |
| 14 | 20 (9) | 145 | 3 d | 50 | 25015 | 50.0% (37%)[b] |
| 15 | 20 (9) | 145 | 3 d | 100 | 37083 | 74.2% (54.0%)[b] |
| 16[a] | 0.1 (9) | 145 | 32 d | 100 | 4557487 | 45.6% |
| 17[d,f] | 20 (9) | 145 | 7 d | 100 | 40889 | 81.7% (55.6%) |
| 18[e,f] | 140 (9) | 145 | 7 d | 100 | 45010 | 90.0% (61.2%)[b] |

Typical reaction conditions are 5 mL glycerol, Ir catalyst, and base (KOH/NaOH weighed and mixed in air). Reaction progress was monitored by gas evolution.
[a]The reaction started with 100 mL glycerol, and was active when quenched.
[b]Isolated yield.
[c]73% based on conversion.
[d]The volume of glycerol is 2 mL in this reaction.
[e]9.3 g glycerol isolated from biodiesel transesterification was used.
[f]NaOH is used in place of KOH.

Heating compound 5 in air with KOH and glycerol results in the selective formation of $H_2$ and lactate (>95%, table 1) with no other products detectable. For example, in a particular run, we observe absence of common side products in glycerol oxidation, such as ethelene glycol, proplene glycol, and 1,3-propane diol by NMR; GC data corroborate the absence of any non-product signals (see supporting information). The robustness of the catalyst is evident from an experiment in which we observe over 1 million turnovers in 8 days (entry 2). This TON is higher than any other homogeneous system reported to date. For example, maximum reported turnover number (TON) for the Crabtree (Ir)7[a] and Beller (Ru)7[b] systems are 30,100 and 256,326, respectively. In a case of a polymeric iridium catalyst, the maximum TON is 124,000.7[c] Further, our system is robust at higher temperatures: at 180° C. the reaction time is shortened from days to hours (entries 5-9). We think that the greater stability and longevity of catalyst 9 is due, in part, to the bidentate architecture of the (pyridyl)carbene. This appears to inhibit ligand scrambling processes, which are observed in the Crabtree system.7[a]

Because these reactions are free of solvent, the medium is very viscous, and the hydroxide base is a partially-dissolved suspension. Upon completion, the reaction mixture comprises mostly lactate salt. Thus, the reaction reaches a solid, unstirrable state at its end, when $H_2$ ceases to evolve. At this point the reaction system is no longer a fluid. The reaction rate slows after ca. 25-30% conversion. We expect that this is a result of the very high viscosity of the reaction mixture limiting mixing and heat flow, rather than chemical deactivation of the catalyst itself. Accordingly, higher catalyst loading will affect higher conversion (compare entries 4 and 11).

While 5 is very robust, we sought a faster and more efficient catalyst. Unlike Crabtree's iridium systems,7[a] our CO-coordinated catalyst precursor (6) shows a mild decrease in catalytic reactivity relative to 5 (compare table 1, entries 4 and 13). We find, however, that the less sterically hindered pyridine-carbene complex 9 enables more rapid reactions than 5. For example, in a typical run with a catalyst loading as low as 20 ppm, over 80% of glycerol can be converted to lactate (entries 17, 18). This conversion is higher than any other homogeneous catalyst in neat glycerol. In a particular run, 9 remains reactive over 32 days delivering a total TON of over 4.5 million (table 1, entry 14). The catalysis is fast at 145° C., with a turn-over-frequency (TOF) of up to $4\times10^4$ $h^{-1}$ in the first hour, and the reaction also takes place at as low as 110° C., with a TOF up to 190 $h^{-1}$ in the first hour. By switching the base to NaOH, the reaction eudiometry kinetic profile appeared a little slower yet steadier through a higher conversion; further the sodium salt enabled more facile product isolation (vide infra).

While our reaction mixtures are suspensions because of the sparing solubility of the hydroxide base, we find that that dehydrogenation catalysis is most likely homogeneous on the basis of (1) physical appearance, (2) clean kinetics, and (3) tolerance of liquid mercury. Quantitative poisoning results are less useful with this reaction: 7,10 surprisingly, 1,10-phenanthroline, a popular catalyst poison that quantitatively deactivates 2 in formic acid dehydrogenation, was found to have no significant impact on the reaction kinetics, even when present in large excess (35 equiv. to [Ir]). We thus find that 9 is tolerant of nitrogen-containing compounds. Triphenylphosphine, another strong poison for homogeneous iridium catalysts, was also used in our glycerol dehydrogenation reaction. With a substoichiometric amount of the poison (0.5 eq. to [Ir]), the reaction rate is within error of the parent. With 600 equiv. of triphenylphosphine to catalyst, the reaction stopped after ca. 3% conversion, 1500 TON.

Key to the value of this contribution is the ability to convert crude output from biodiesel production to value added material. Along these lines, we have demonstrated the conversion of soybean oil to fatty acid methyl esters (FAMEs, a biodiesel component) and crude glycerol, then further conversion of the resulting crude glycerol to lactate salt. Thus, we treated 100 mL (93.2 g) Wesson soy bean oil with sodium methoxide and successfully isolated 100 mL of FAMEs and 9.3 g glycerol, the latter with >95% NMR purity. With no purification other than solvent removal, this glycerol was catalytically converted to an isolated aliquot of 5.6 g of lactic acid.

Of further importance to the utility of this technology is a facile route to convert the crude lactate salt to rac- and meso-lactide monomers for use in poly(lactic acid) synthesis. We have achieved this using a simple pH extraction followed by known transformations for lactide preparation (see supporting information). Thus, lactic acid can be thermally oligomerized directly from our concentrated extract to yield a prepolymer, which can then be treated with SnO to convert the material to crude rac- and meso-lactide mixture. Recrystallization of lactides mixture successfully afforded rac-lactide with high purity and a yield of 69% from crude lactic acid, with a small fraction of meso-lactide available from the mother liquor.

Beyond glycerol conversion, we find that 9 is a catalyst for general alcohol dehydrogenation. For example, we can effect methanol dehydrogenation in a refluxing alkaline solution of 25% aqueous methanol. From the reaction solution, we evolve hydrogen with 461 turnovers of $H_2$. in 12 hours and isolate a crystal $Na_2CO_3.NaHCO_3.H_2O$ as the by-product.

Although we do not yet have a complete understanding of the mechanism of our reaction, we do have a working model (scheme 2). The fate of the organic species is known:[11] an initial, rate-determining dehydrogenation of either of the alcohol positions of glycerol enables facile dehydration and rearrangement according to scheme 2a. We know that catalytic oxidation is the slow step in this sequence for us, because we see no organic species other than glycerol and lactate >1% by NMR under the catalytic conditions. Further, conversion of glyceraldehyde to lactate is known to be rapid at temperatures as low as 25° C. in alkali media.[12]

More interesting to us is the mechanism of the catalytic oxidation cycle (scheme 2b). We propose that the active catalytic species is monomeric: unlike species 1, species 5 and 9 do not undergo dimerization in the presence of buffered formic acid and lack 1's reactivity in formic acid dehydrogenation. Particularly, under comparable conditions (140 ppm [Ir], 280 ppm base in 2 mL $HCO_2H$, 3.5 h), a 1-catalyzed reaction undergoes >97% conversion of formic acid, whereas the conversion is below 3% when 5 or 9 is used. Conversely, 1 does not lead to efficient glycerol to lactate conversion under the conditions used in table 1. In a representative example, when 200 ppm 1 is heated with glycerol and hydroxide, lactate is formed with <5% conversion at the point that catalyst turnover ceases.

Unfortunately, study of this mechanism is frustrated by a complicated network of exchangeable protons and rapidly substituting labile oxygen ligands. We believe that catalysis initiates from 9 by solvent displacement of 9's cyclooctadiene ligand, which we observe to be rapid, even at room temperature. We then believe that our ligand is deprotonated to make a charge neutral complex. This deprotonated form of 9 is deeply purple in color, which is observed at room temperature only when 9 is treated with base in the absence of glycerol.[13] If 9 is treated with base in the presence of glycerol, the red solution of 9 assumes a light yellow color, which is characteristic of our working catalyst. We therefore expect that the deprotonated catalyst cleaves glycerol's O—H bond cooperatively, rather than by simple proton transfer, because we observe that 9 is more acidic than glycerol. One possibility for this O—H cleavage is illustrated as 10. We think that the catalyst rests as a mixture of coordination adducts of deprotonated glycerol, which are sketched as 11.

We used dehydrogenation of 1-phenylethanol as simplified model to probe reaction kinetics. The turnover-limiting step of catalysis appears to be β-hydride elimination from an iridium alkoxide such as 11. Three key data points support this finding: (1) we observe a first order dependence on the concentration of the alcohol substrate, which is inconsistent with rate-determining H—H bond formation or $H_2$ loss. (2) We find an insignificant $KIE_{OH/OD}$ of 1.1(1), which is inconsistent with kinetic relevance of any transition state involving O—H cleavage or H—H formation. (3) A more electron rich substrate, 1-(4-methoxyphenyl)ethanol, dehydrogenates with a rate ca. 3 times faster than 1-phenylethanol. This indicates a negative (electrophilic) Hammett reaction parameter, which is better fit to β-hydride elimination than H—H bond formation or ligand substitution as a turnover-limiting step.[14]

We do not know which hydroxyl group of glycerol is oxidized: in two parallel experiments in which aqueous solutions of $^i$PrOH and $^n$PrOH are dehydrogenated with 9 and base, we see rates that are identical within error. Either of these β-hydride elimination reactions should form an iridium hydride, which is sketched as 12 in scheme 2. Hydrogen is likely released from hydride 12 by protonation with an alcohol O—H group. While we see no evidence for an iridium hydride under the catalytic conditions, we can observe a diversity of iridium hydride species at room temperature when 9 is treated with a stoichiometric portion of isopropanol in alkaline solution. We therefore find that an iridium hydride is a plausible intermediate, although not a resting state of catalysis.

In conclusion, we present here a high-utility technique for the conversion of crude glycerol to value-added lactides based on the oxidative conversion of glycerol to lactate. This oxidation utilizes a structurally novel iridium catalyst supported by a bidentate (pyridylmethyl)imidazolium carbene ligand. The new catalyst system enables unprecedented efficiency, longevity, and conversion in the oxidation of glycerol to lactic acid and thus enables a very practical alternative to fermentation compared to those currently available for lactic acid preparation. The reactive mechanism of this new system is proposed on the basis of experimental evidence: oxidation involves turnover-limiting β-hydride elimination to form dihydroxyacetone, which is converted rapidly to lactate. Investigations of the broader utility of 9 and its mechanism for alcohol dehydrogenation are underway in our laboratory.

Supplemental Materials

S1. Materials and Methods

All air and water sensitive procedures were carried out either in a Vacuum Atmosphere glove box under nitrogen (2-10 ppm $O_2$ for all manipulations) or using standard Schlenk techniques under nitrogen. Dichloromethane-$d_2$, methanol-$d_4$, $D_2O$, acetonitrile-$d_3$, benzene-$d_6$ and any other NMR solvents were purchased from Cambridge Isotopes Laboratories. Dichloromethane-$d_2$, acetonitrile-$d_3$, benzene-$d_6$ and methanol-$d_4$, THF-$d_8$ are carefully dried prior to use. Dichloromethane-$d_2$ is stirred over $CaH_2$ for 1 day then vapor transferred into a dry flask; acetonitrile-$d_3$ is stirred over $CaH_2$ for 1 day then vapor transferred into a dry flask; benzene-$d_6$ is stirred over Na/benzophenone for 1 day then vapor transferred into a dry flask; methanol-$d_4$ is stirred over Na for 1 day then vapor transferred into a dry flask; THF-$d_8$ is stirred over Na/benzophenone for 1 day then vapor transferred into a dry flask. Dichloromethane, ethyl ether, THF and hexanes are purchased from VWR and dried in a J. C. Meyer solvent purification system with alumina/copper (II) oxide columns; bulk methanol in methyl FAME synthesis was dried by stirring over activated molecular sieves over night; chloro(1,5-cyclooctadiene)iridium(I) dimer (Strem), sodium trifluoromethanesulfonate (Sigma-Aldrich), potassium tert-butoxide (Sigma-Aldrich) were purged with nitrogen and stored under nitrogen atmosphere; glycerol (EMD Millipore) was used as received; Wesson vegetable oil was purchased from a local grocery store and used without purification; pyridine-imidazolium ligands and corresponding silver carbenes were synthesized using a literature procedure.[1]

NMR spectra were recorded on a Varian VNMRS 500 or VNMRS 600 spectrometer, processed using MestroNova. All chemical shifts are reported in units of ppm and referenced to the residual $^1H$ or $^{13}C$ solvent peak and line-listed according to (s) singlet, (bs) broad singlet, (d) doublet, (t) triplet, (dd) double doublet, etc. $^{13}C$ spectra are delimited by carbon peaks, not carbon count. $^{19}F$ chemical shifts are referenced to a trichlorofluoromethane external (coaxial insert tube) standard (0 ppm). Air-sensitive NMR spectra were taken in 8" J-Young tubes (Wilmad or Norell) with Teflon valve plugs. MALDI mass spectra were obtained on an Applied Biosystems Voyager spectrometer using the evaporated drop method on a coated 96 well plate. The matrices used for MALDI are 2,5-dihydroxybenzoic acid or anthracene. In a standard preparation, ca. 1 mg analyte and ca. 10 mg matrix was dissolved in methanol and spotted on the 96-well MALDI plate with a glass capillary. Infrared spectra were recorded on Bruker OPUS FTIR spectrometer. X-ray crystallography data were obtained on a Bruker APEX DUO single-crystal diffractometer equipped with an APEX2 CCD detector, Mo fine-focus and Cu micro-focus X-ray sources. Elemental analysis data were obtained on a Thermo Flash 2000 CHNS Elemental Analyzer. Lyophilization was accomplished with a Millrock benchtop freeze dryer. FID-GC data were collected on a PerkinElmer Clarus 680 FID GC. Data were collected with use of TotalChrom Navigator software and graphed was plotted with Microsoft Excel.

Dehydrogenation Procedures

Figure 3B:
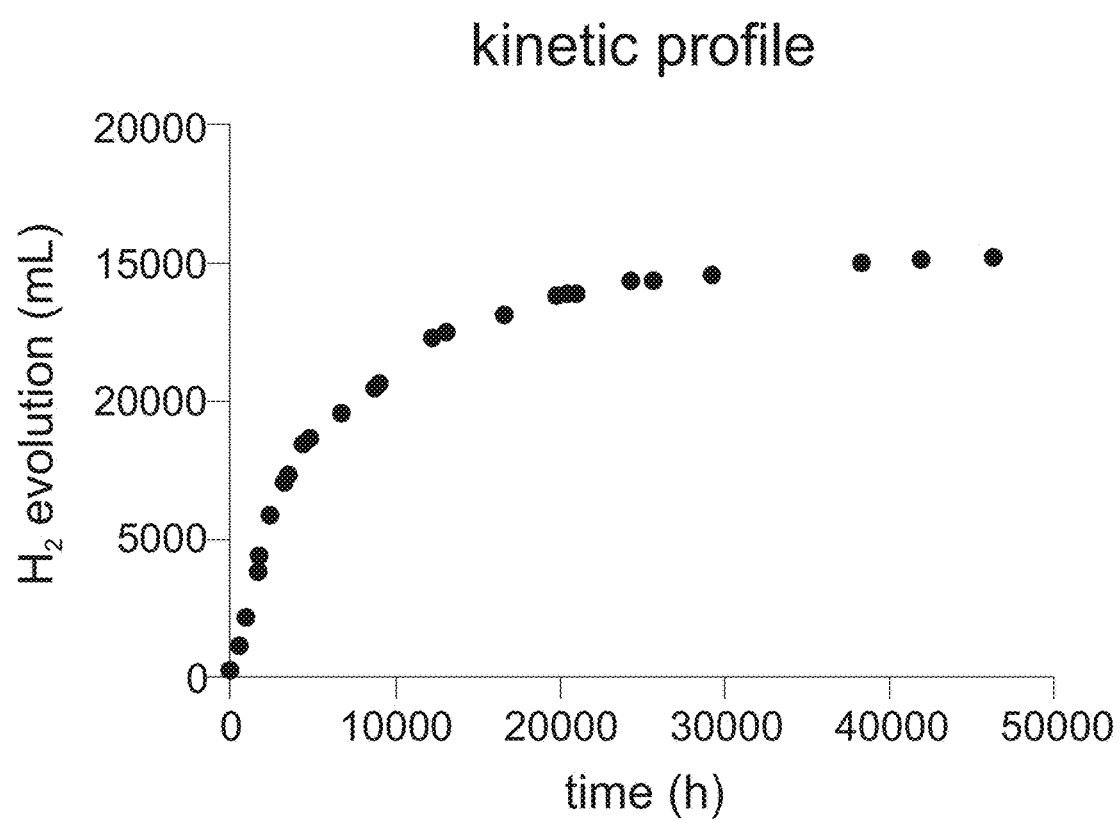

The iridium catalysts for glycerol dehydrogenation are stored in a glovebox for long term purpose. In a typical reaction, iridium catalyst, base (i.e. KOH, NaOH), are weighed outside the glovebox, added to a round bottom flask equipped with a magnetic stir bar. Glycerol is measured and added to the same flask with a disposable plastic syringe. The flask then is connected to an air condenser, which has a 8 mm Tygon tubing gas outlet immersed in a water eudiometer (inverted burette, FIG. 3). The reaction progress is monitored by eudiometry. An oil bath is used for reactions at 145° C.; a sand bath is used for reactions at 180° C. Bath temperature is monitor using an alcohol thermometer. Normally <±2.5° C. temperature fluctuation is observed for oil baths, and <±10° C. fluctuation is observed for sand baths.

S2. Synthetic Procedures and Characterization Data

Note: all the procedures for syntheses of iridium complexes are performed in the glovebox.

Complex 5:

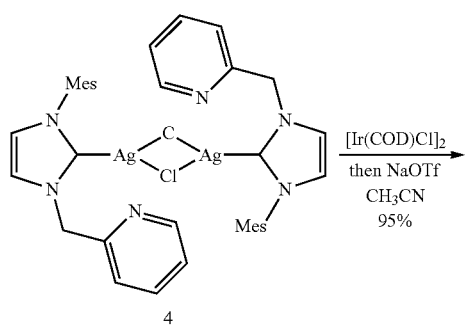

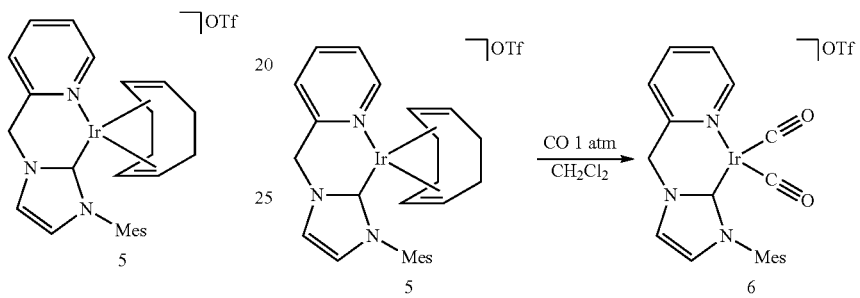

In the glovebox under nitrogen, in a 100 mL in a Schlenk flask, dichloro-di(1-(2,4,6-trimethylphenyl)-3-(2-picolyl)-imidazol-2-ylidene)-disilver(I)[1] 4 (251 mg, 0.298 mmol) was added in small portions to a stirring solution of chloro (1,5-cyclooctadiene)Iridium(I) dimer (200.0 mg, 0.298 mmol) in 20 mL dry acetonitrile. After 30 minutes, sodium trifluoromethanesulfonate (102.5 mg, 0.596 mmol) was also added to the mixture. After stirring for another 30 minutes, the solution was filtered through a dry pad of celite to remove the sodium chloride byproduct. The solvent was evaporated under reduced pressure to yield a red glassy solid. This red solid was dissolved in 10 mL dry dichloromethane, and 20 mL dry hexanes was added to the solution to facilitate a precipitation. A red crystalline solid was acquired and dried under vacuum (400 mg, 93%). This sample was later determined to be spectroscopically pure under NMR. Slow recrystallization from dichloromethane and hexanes produced crystals suitable for X-ray crystallography.

$^1$H NMR (600 MHz, methylene chloride-$d_2$) δ 8.50 (ddd, J=7.7, 1.6, 0.8 Hz, py 1H), 8.08 (ddd, J=7.8, 1.6, 0.7 Hz, py 1H), 8.01 (td, J=7.7, 1.5 Hz, py 1H), 7.70 (d, J=1.9 Hz, Im 1H), 7.48 (ddd, J=7.4, 5.6, 1.5 Hz, py 1H), 7.04 (s, mesityl-ar 1H), 7.00 (s, mesityl-ar 1H), 6.88 (d, J=1.9 Hz, Im 1H), 5.77 (s, methylene 1H), 5.74 (s, methylene 1H), 4.15 (s, COD sp$^2$ 1H), 4.07 (s, COD sp$^2$ 1H), 3.92 (s, COD sp$^2$ 1H), 3.21 (s, COD sp$^2$ 1H), 2.37 (s, mesityl-para-methyl 3H), 2.25-1.85 (m, COD sp$^3$ 6H), 2.06 (s, mesityl-ortho-methyl 3H), 1.90 (s, mesityl-ortho-methyl 3H), 1.63 (s, COD sp$^3$ 1H) 1.47 (s, COD sp$^3$ 1H).

$^{13}$C NMR (151 MHz, methylene chloride-$d_2$) δ 174.64 (carbene C), 153.38 (py), 151.40 (py), 140.51 (py), 140.16 (mesityl), 135.32 (py), 129.68 (mesityl-ar), 129.46 (mesityl-ar), 126.88 (mesityl-ar), 123.51 (Im), 122.54 (Im), 86.04 (COD sp$^2$), 82.80 (COD sp$^2$), 66.08 (COD sp$^2$), 64.43 (COD sp$^2$), 55.34 (py-CH2), 34.99 (COD sp$^3$), 31.89 (COD sp$^3$), 31.44 (COD sp$^3$), 28.17 (COD sp$^3$), 21.23 (mesityl-CH$_3$), 19.13 (mesityl-CH$_3$), 17.94 (mesityl-CH$_3$).

$^{19}$F NMR (470 MHz, methylene chloride-$d_2$) δ −79.43.

Elemental Analysis (CHNS) calc'd for $C_{27}H_{31}F_3IrN_3OS$: C, 44.62; H, 4.30; N, 5.78; S, 4.41. Found: C, 44.55; H, 4.24; N, 5.84; S, 4.24.

IR (thin film/cm$^{-1}$) ν 3584, 3441, 2918, 2849, 2362, 1734, 1608, 1444, 1411, 1263, 1223, 1070, 1030, 853, 804, 636, 628.

MS (MALDI) calc'd for $[C_{26}H_{31}IrN_3]^+$ 578.2, found 577.9.

Complex 6

In the glovebox under nitrogen, 5 (330 mg, 0.453 mmol) was dissolved in 15 mL CH$_2$Cl$_2$ in a 100 mL Schlenk flask. The flask was sealed and frozen in liquid nitrogen outside the glovebox. The headspace of the flask was evacuated for 1 minute under dynamic vacuum whilst the solution remains frozen, then the headspace was refilled with 1 atm CO gas. The solution was allowed to warm up to room temperature and was further stirred for 30 minutes. During this time, the reaction turned from red to yellow. Slowly adding 30 mL hexanes afforded a yellow crystalline solid, which was dried under vacuum (300 mg, 98%). Compound 6 is stable under air.

$^1$H NMR (600 MHz, methylene chloride-$d_2$) δ 8.83 (dd, J=5.7, 1.5 Hz, py 1H), 8.30 (dd, J=7.9, 1.4 Hz, py 1H), 8.19 (ddd, J=7.8, 6.5, 1.3 Hz, py 1H), 7.99 (dd, J=2.0, 0.9 Hz, imi 1H), 7.59 (td, J=6.5, 1.1 Hz, py 1H), 7.08 (dd, J=1.9, 0.9 Hz, imi 1H), 7.05 (s, mesityl-ar 2H), 5.77 (s, methylene 2H), 2.38 (s, mesityl-para-methyl 3H), 2.00 (s, mesityl-ortho- 6H).

$^{13}$C NMR (151 MHz, methylene chloride-$d_2$) δ 182.71 (CO), 173.05 (carbene C), 169.67 (CO), 156.68 (py), 154.71 (py), 143.23 (py), 141.09 (mesityl), 135.87 (py), 134.40 (mesityl), 129.84 (mesityl), 128.50 (py), 127.04 (mesityl), 124.25 (Im), 123.78 (Im), 54.52 (py-CH$_2$), 21.28 (mesityl-CH$_3$), 18.38 (mesityl-CH$_3$).

$^{19}$F NMR (470 MHz, methylene chloride-$d_2$) δ −79.4.

Elemental Analysis (CHNS) Anal. calc'd for $C_{21}H_{20}F_3IrN_3O_5S$: C, 37.39; H, 2.84; N, 6.23; S, 4.75. Found: C, 37.44; H, 3.02; N, 6.34; S, 4.34.

IR (thin film/cm$^{-1}$) ν 3442, 3126, 2921, 2077 (CO), 2011 (CO), 1612, 1488, 1451, 1420, 1364, 1309, 1225, 1157, 1072, 704.

MS (MALDI) calc'd for $[C_{20}H_{19}IrN_3O_2]^+$ 526.1, found 525.9.

Complex 9

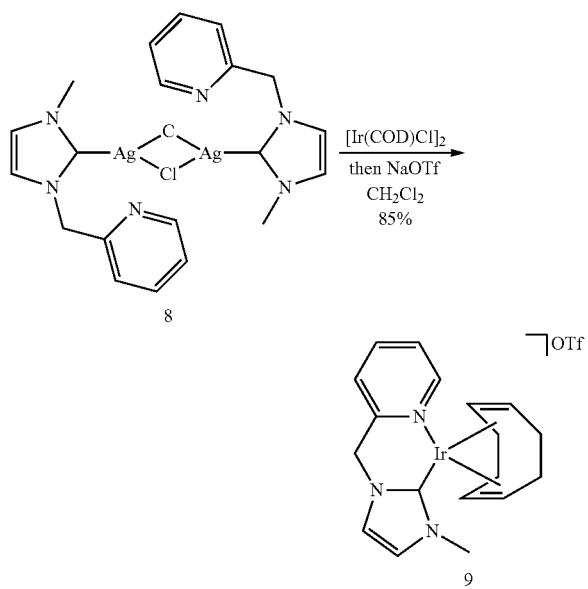

In the glovebox under nitrogen, in a 100 mL in a Schlenk flask, dichloro-di(1-methyl-3-(2-picolyl)-imidazol-2-ylidene)-disilver(I) 4 (89.5 mg, 0.141 mmol) was added in small portions to a stirring solution of chloro(1,5-cyclooctadiene)Iridium(I) dimer (95.0 mg, 0.141 mmol) in 20 mL dry dichloromethane. After 30 minutes, sodium trifluoromethanesulfonate (49 mg, 0.285 mmol) was also added to the mixture. After stirring for another 30 minutes, the solution was filtered through a dry pad of celite to remove the sodium chloride byproduct. The solvent was evaporated under reduced pressure to yield a red glassy solid. This red solid was dissolved in 5 mL dry dichloromethane, and 10 mL dry hexanes was slowly added to the solution to facilitate a precipitation. A red crystalline solid was acquired and dried under vacuum (150 mg, 85%). This sample was later determined to be spectroscopically pure under NMR. Slow recrystallization from dichloromethane and hexanes produced crystals suitable for X-ray crystallography. 9 is mildly air-sensitive and is stored under $N_2$.

$^1H$ NMR (600 MHz, methylene chloride-$d_2$) δ 8.55 (d, J=5.2 Hz, py 1H), 7.79 (t, J=7.7 Hz, py 1H), 7.64 (d, J=7.9 Hz, py 1H), 7.33 (t, J=6.4 Hz, py 1H), 7.14 (d, J=2.0 Hz, imi 1H), 6.89 (d, J=2.0 Hz, imi 1H), 5.74 (d, J=15.0 Hz, methylene 1H), 5.56 (d, J=14.8 Hz, methylene 1H), 4.48 (s, COD $sp^2$ 1H), 4.28 (s, COD $sp^2$ 1H), 3.89 (s, imi-methyl 3H), 3.48 (s, COD $sp^2$ 1H), 3.29 (s, COD $sp^2$ 1H), 2.33 (s, COD $sp^3$ 2H), 2.14 (s, COD $sp^3$ 2H), 1.81 (s, COD $sp^3$ 3H), 1.61 (s, COD $sp^3$ 1H).

$^{13}C$ NMR (151 MHz, methylene chloride-$d_2$) δ 174.54 (carbene C), 153.26 (py), 151.42 (py), 140.12 (py), 137.58 (py), 126.40 (py), 123.16 (Im), 122.31 (Im), 79.57 (COD $sp^2$), 75.42 (COD $sp^2$), 65.59 (COD $sp^2$), 58.86 (COD $sp^2$), 55.30 (py-$CH_2$), 37.87 (Im-$CH_3$), 33.38 (COD $sp^3$), 33.24 (COD $sp^3$), 30.14 (COD $sp^3$), 29.77 (COD $sp^3$).

$^{19}F$ NMR (470 MHz, methylene chloride-$d_2$) δ −79.41.

Elemental Analysis (CHNS) Anal. calc'd for $C_{19}H_{23}F_3IrN_3O_3S$: C, 36.65; H, 3.72; N, 6.75; S, 5.15. Found: C, 37.04; H, 3.75; N, 6.41; S, 4.97.

MS (MALDI) calc'd for $[C_{18}H_{23}IrN_3]^+$ 474.2, found 473.9.

S3. Initial Condition Optimization

Identification of Reaction Conditions

With reference to FIG. 3A, a reaction system 10 for the conversion of glycerol to lactic acid is provided. In a typical reaction, iridium catalyst (20 ppm with regard to glycerol), base (i.e. KOH, NaOH, 1 eq. to glycerol), are weighed outside the glovebox in air, added to a round bottom flask 12 equipped with a magnetic stir bar and positioned above hot/stir plate 14. Glycerol (5 mL) is measured and added to the same flask with a disposable plastic syringe. The flask then is connected to a short path distilling head 16 (e.g., an air condenser), which has a 8 mm Tygon tubing gas outlet 18 put in a water eudiometer (inverted burette 20 position in a water filler beaker 22, FIG. 3A). The flask is then placed in an oil bath set to 145° C., and the reaction progress is monitored by eudiometry. The results are summarized as following.

TABLE 1

Initial conditions attempted for a conversion of glycerol to lactic acid.

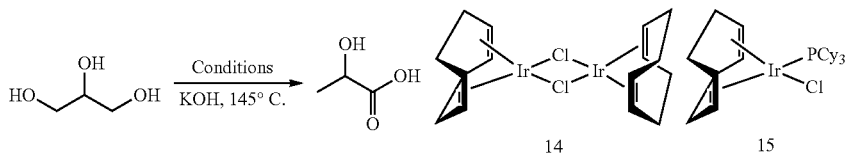

| entry | Catalyst | Temp. (° C.) | Time | Base or Acid | TON | Conversion |
|---|---|---|---|---|---|---|
| 1 | — | 145 | 1 d | 0.5 eq. KOH | — | <1% |
| 2 | 20 ppm 5 | 145 | 1 d | 10 mol % TFA | — | <1% |
| 3 | 100 ppm 5 | 145 | 1 d | — | — | <1% |
| 4 | 20 ppm 5 | 145 | 1 d | 0.5 eq. Ca(OH)$_2$ | 899 | 1.8% |
| 5 | 20 ppm 5 | 145 | 1 d | 0.5 eq. CaO | — | <1% |
| 6 | 20 ppm 5 | 145 | 1 d | 10 mol % DBU | — | <1% |
| 7 | 20 ppm 5 | 145 | 4 d | 1 eq. KOtBu | 16777 | 33.6% |
| 8 | 50 ppm 14 | 145 | 3 d | 0.5 eq. KOH | 839[a] | 8.4% |
| 9 | 50 ppm 15 | 145 | 3 d | 0.5 eq. KOH | 1198 | 6.0% |

[a]TON calculated based on iridium atom.

GC Analysis of Products

Figure 4:
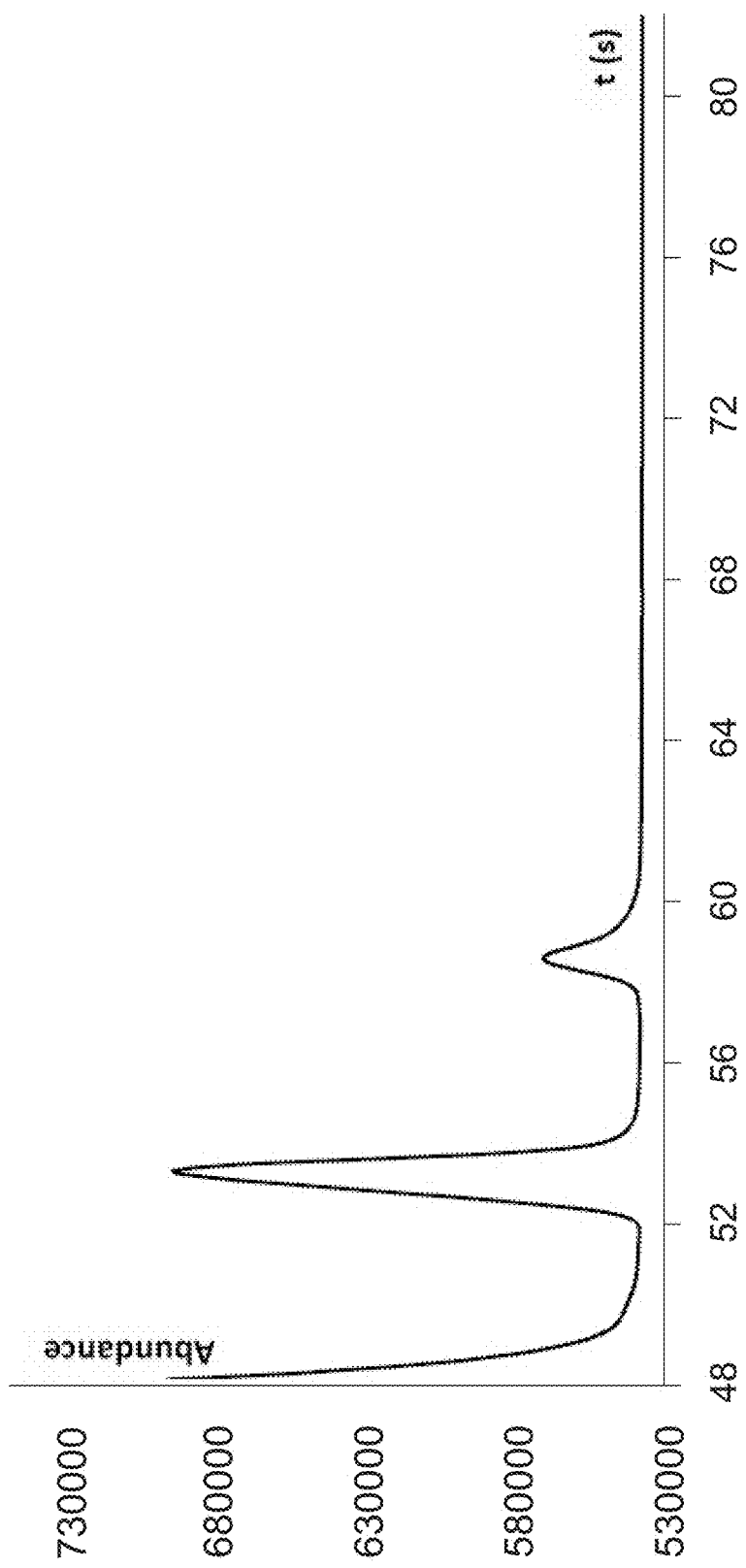
FIG. 4. FID-GC analysis of a representative crude reaction mixture showing lactic acid (53.2) and glycerol (58.5). Lactides (71.7, 72.3), ethylene glycol (48.6), 1,2-propane diol (49.8), and 1,3-propane diol (51.6) are absent.

Typical runs of glycerol to lactic acid conversion (including acidification and extraction) tend to have exclusive selectivity: 1H NMR data show only lactic acid and glycerol. For example, see FIGS. 6-8 below. This observation is corroborated by GC analysis. For example, we ran a representative trial of glycerol conversion to completion and the resulting solid was treated with 25 ml of 1M HCl for 20 minutes. The resulting solution was extracted with ethyl ether (3 times, 10 mL) and concentrated under reduced pressure to approximately 0.1 mL. 10 mg of that solution was dissolved in 2 ml of methanol and analyzed by FID-GC. The resulting FID-GC spectrum (FIG. 4) shows only lactic acid and glycerol. Common impurities in glycerol conversion (rac- and meso-lactides, ethylene glycol, 1,2-propane diol, and 1,3-propane diol) are systematically absent, as determined by analyzing authentic samples of these in separate runs.

S4. Homogeneity Tests

Figure 6:
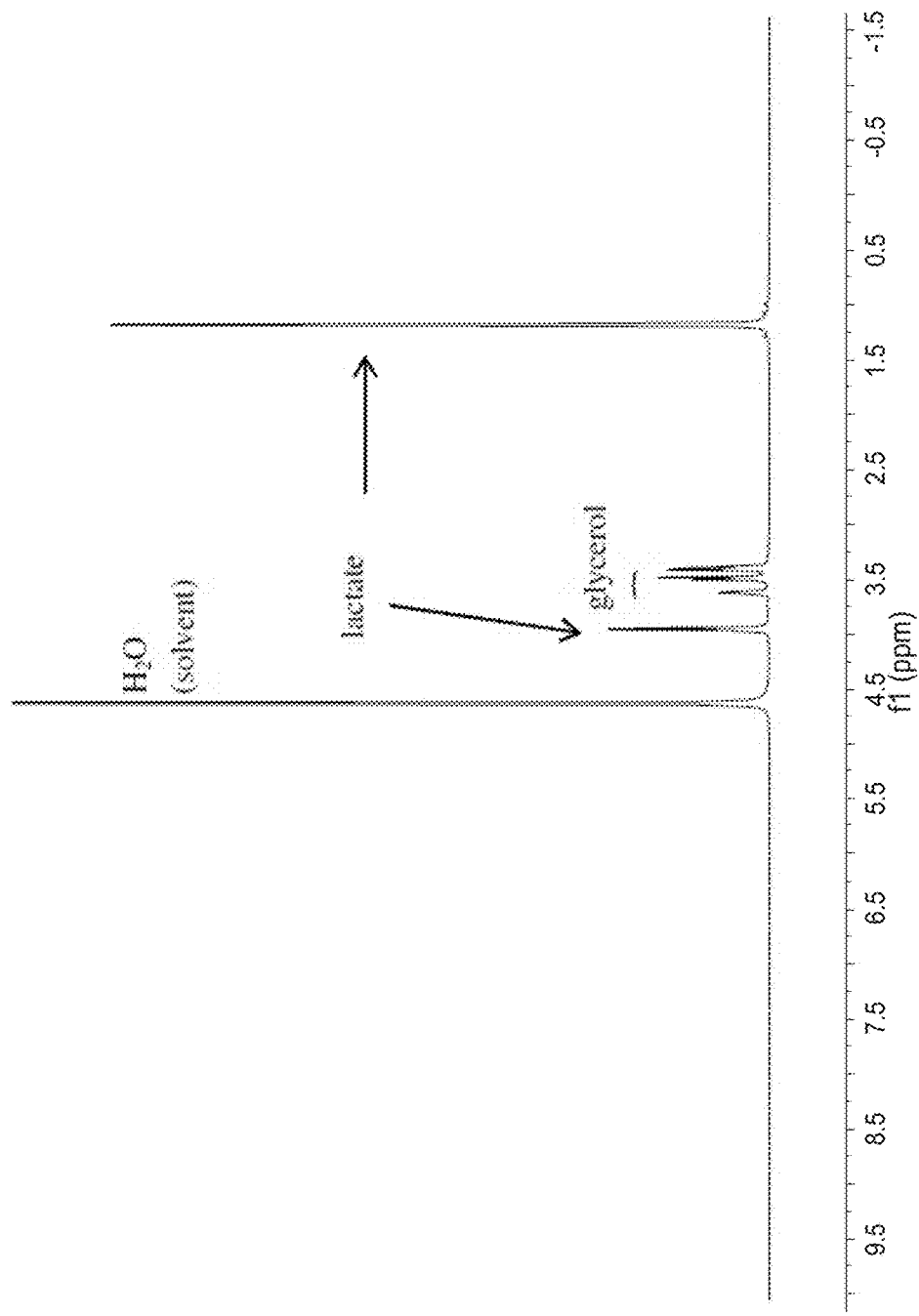
FIG. 6. A snapshot of reaction mixture after 3 days.

In these reactions, based on our typical conditions (5 mL glycerol, iridium catalyst 9, 20 ppm; base KOH, 0.5 eq. to glycerol at 145° C.) mercury drops, phenanthroline (phen) poison or PPh$_3$ poison are also added to the reaction flask in parallel runs. The reactions were monitored by eudiometry. The results are summarized in table 2. For a typical kinetic profile, see FIG. 3B.

bath set to 145° C., and the reaction progress is monitored by eudiometry and $^1$H-NMR. A snapshot of the reaction mixture is taken in $^1$H-NMR, which shows well-controlled selectivity for lactate (FIG. 6).

Figure 7:
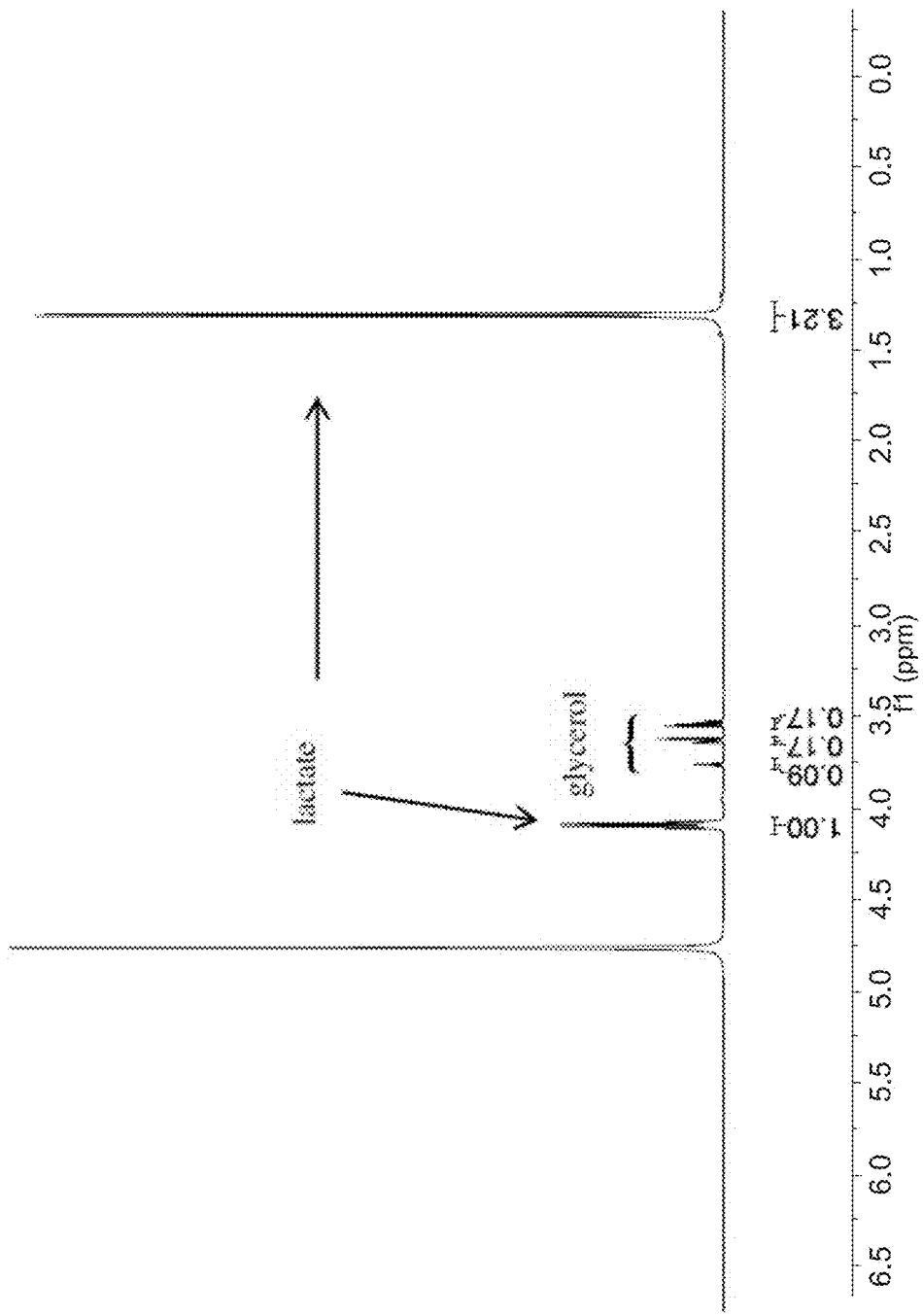
FIG. 7. $^1$H NMR of reaction mixture after 7 days, at 90% conversion. The solvent is $D_2O$.

After 7 days, eudiometry shows that the reaction has ca. 90% conversion. The reaction flask was cooled to room temperature. $^1$H NMR shows only lactate product and a small amount of glycerol (FIG. 7).

Figure 8:
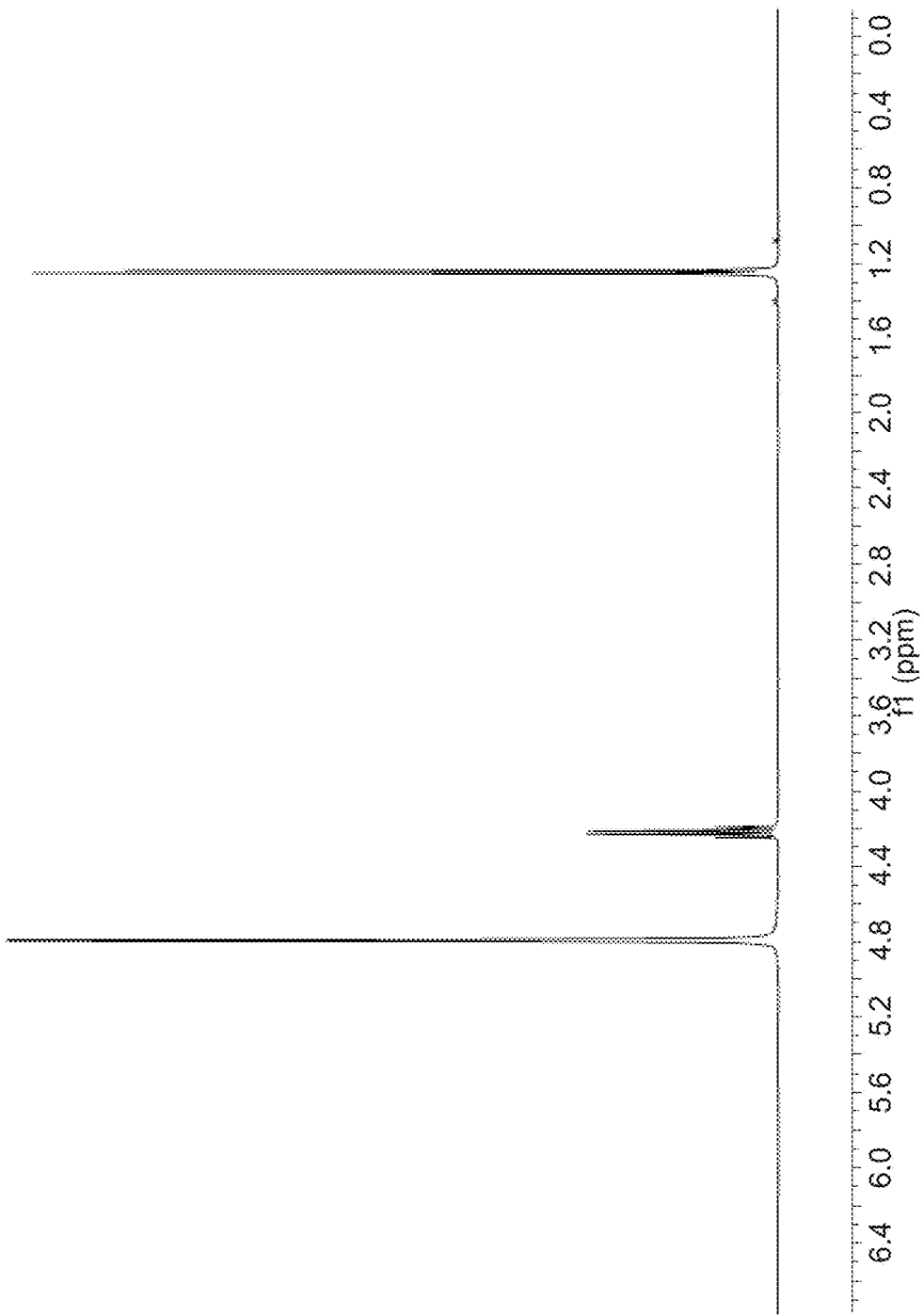
FIG. 8. $^1$H NMR of isolated lactic acid in $D_2O$.

We find that using NaOH instead of KOH yielded much more soluble solid at the end of the reaction, which enabled a much facile isolation of lactic acid. Accordingly, conc. hydrochloric acid (1 M, 70 mL) was added the reaction flask until the pH was <1, then the solution was extracted with ethyl acetate (25 mL×5). The organic solvent was evaporated under a constant flow of air, a colorless liquid left at the bottom of the flask was identified as NMR pure lactic acid (5.6 g, 61.5%) (FIG. 8).

S6. Lactide Synthesis

The reactions for lactic acid to lactide conversion are based on known procedures.[2]

From Lactic Acid to Polylactic Acid Oligomers

In a typical run, 2.50 g of lactic acid obtained from the previously described extractions is weighed in air and added to a round bottom flask equipped with a magnetic stirring bar. The flask is connected to a Dean-Stark trap with condenser on top of it. The flask is then placed in a wax bath

TABLE 2

Homogeneity test using various poisons.

| entry | Poison | equiv. to [Ir] | Time | TON | Conversion |
|---|---|---|---|---|---|
| 1 | — | — | 1 d | 18125 | 36.3% |
| 2 | Hg(1) | — | 1 d | 18574 | 37.1% |
| 3 | 250 ppm phen | 15 | 1 d | 17376 | 34.8% |
| 4 | 700 ppm phen | 35 | 1 d | 18724 | 37.4% |
| 5 | 10 ppm PPh$_3$ | 0.5 | 1 d | 14080 | 28.2% |
| 6 | 1.2 mol % PPh$_3$ | 600 | 3 h | 1498 | 3.0% |

S5. Conversion of Soybean Oil to FAMEs and Lactic Acid

From Soybean Oil to FAMEs and Glycerol

Figure 5:
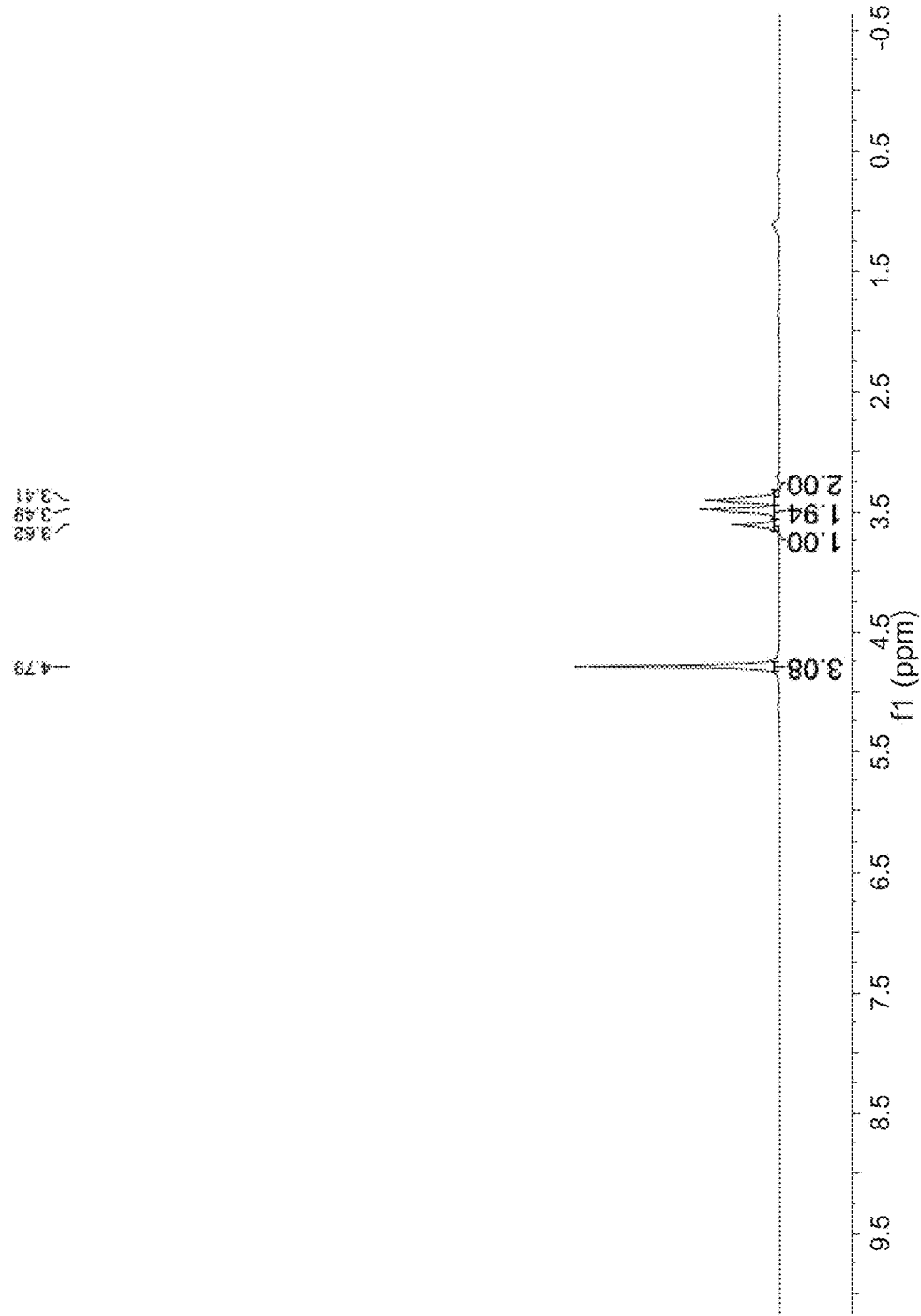
FIG. 5. $^1$H-NMR spectrum of the glycerol isolated from a transesterification product of Wesson soybean oil.

In a typical reaction soybean oil (100 mL, 93 g) is added to a stirring solution of dilute NaOMe (20 mg) in dry methanol (100 mL) under nitrogen. The mixture is heated in a water bath set to 50° C. for 5 hours. After stirring is stopped and the mixture is returned to room temperature, the reaction mixture settles to two layers. On the top is the SoyFAME layer, in it ca. 100 mL of biodiesel material. The bottom is a methanol solution of glycerol, which was subsequently concentrated by rotary evaporation, then dried on a lyophilizer overnight, and finally on a high-vacuum Schlenk line to afford 9.3 g of NMR pure (>95%) glycerol. We believe that the glycerol is mostly free of methanol or water. For $^1$H-NMR of the glycerol product, see FIG. 5.

From Glycerol to Lactic Acid

Figure 9:
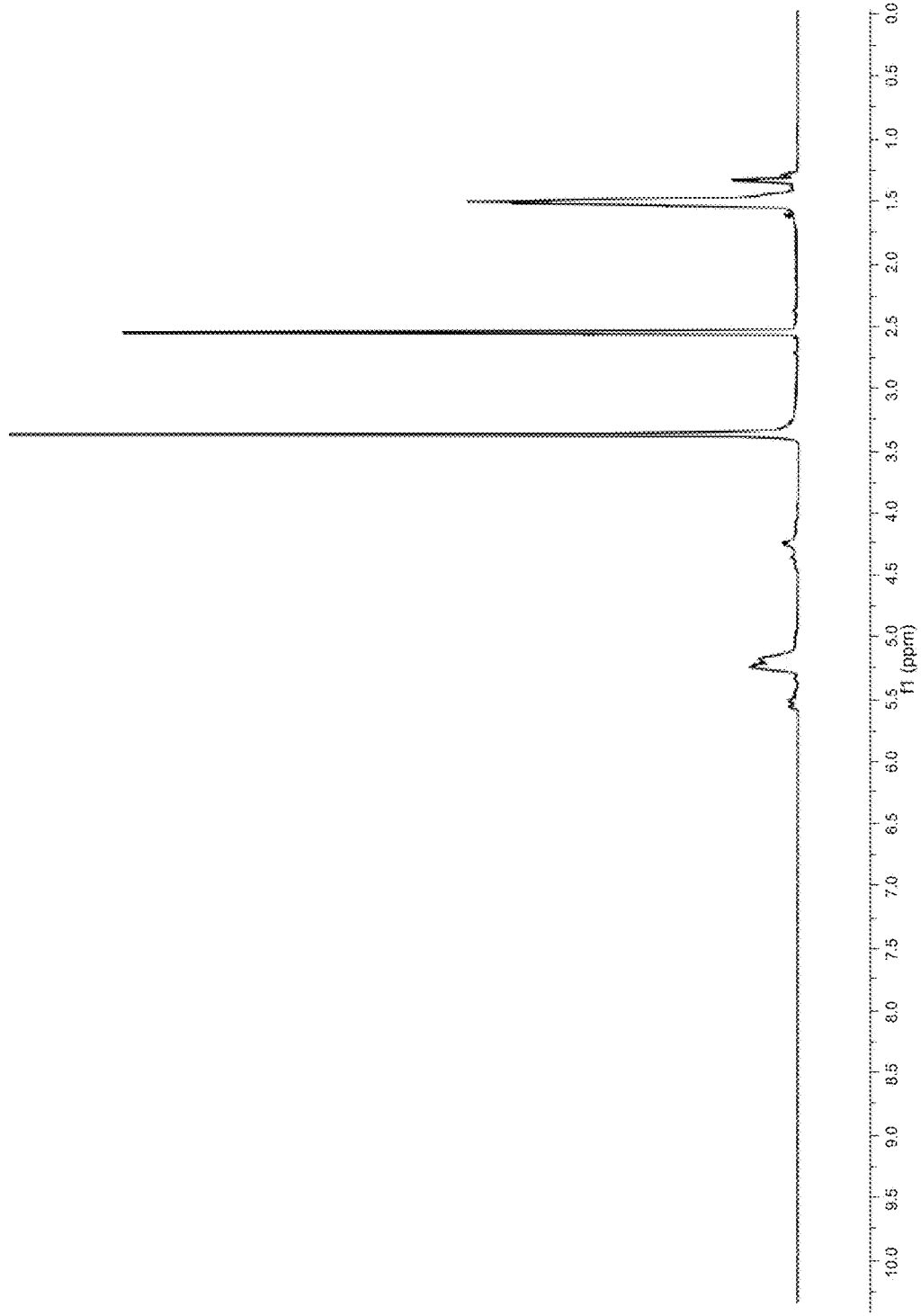
FIG. 9. $^1$H NMR of polylactic acid oligomer in DMSO-$d_6$.
Figure 10:
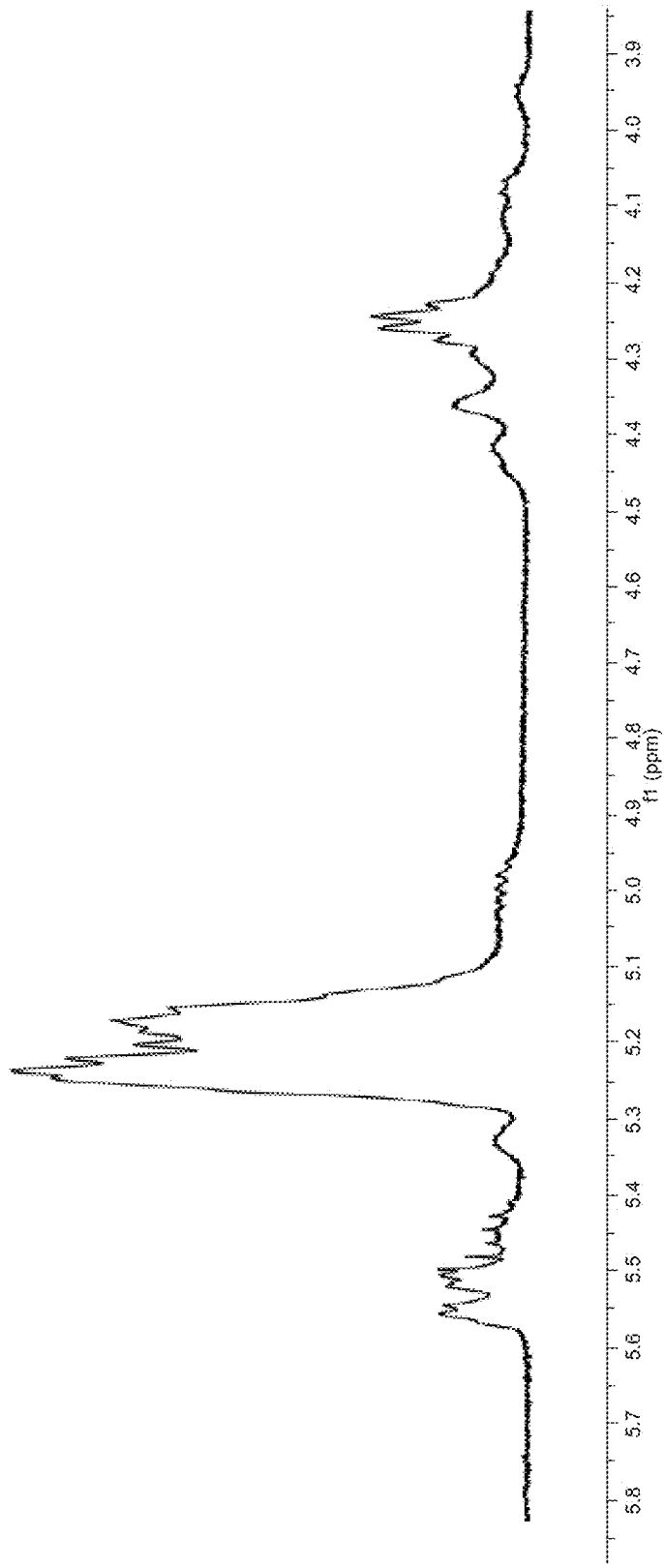
FIG. 10. $^1$H NMR "zoom-in" on "methine" region of the polylactic acid oligomer.

Iridium catalyst 9 (5.8 mg, 140 ppm to glycerol) and NaOH (4.0 g, 1.0 eq. to glycerol), are weighed in air and added to a round bottom flask equipped with a magnetic stir bar. Glycerol (9.3 g from soybean oil, above) is added to the same flask. The flask then is connected to a short path distilling head, which has a 8 mm Tygon tubing gas outlet put in a water eudiometer. The flask is then placed in an oil set to 210° C. The reaction is carried out under nitrogen for 6 hours. FIG. 9 provides $^1$H NMR of polylactic acid oligomer in DMSO-d$_6$ while FIG. 10. $^1$H NMR "zoom-in" on "methine" region of the polylactic acid oligomer.

Lactide Formation

Figure 11:
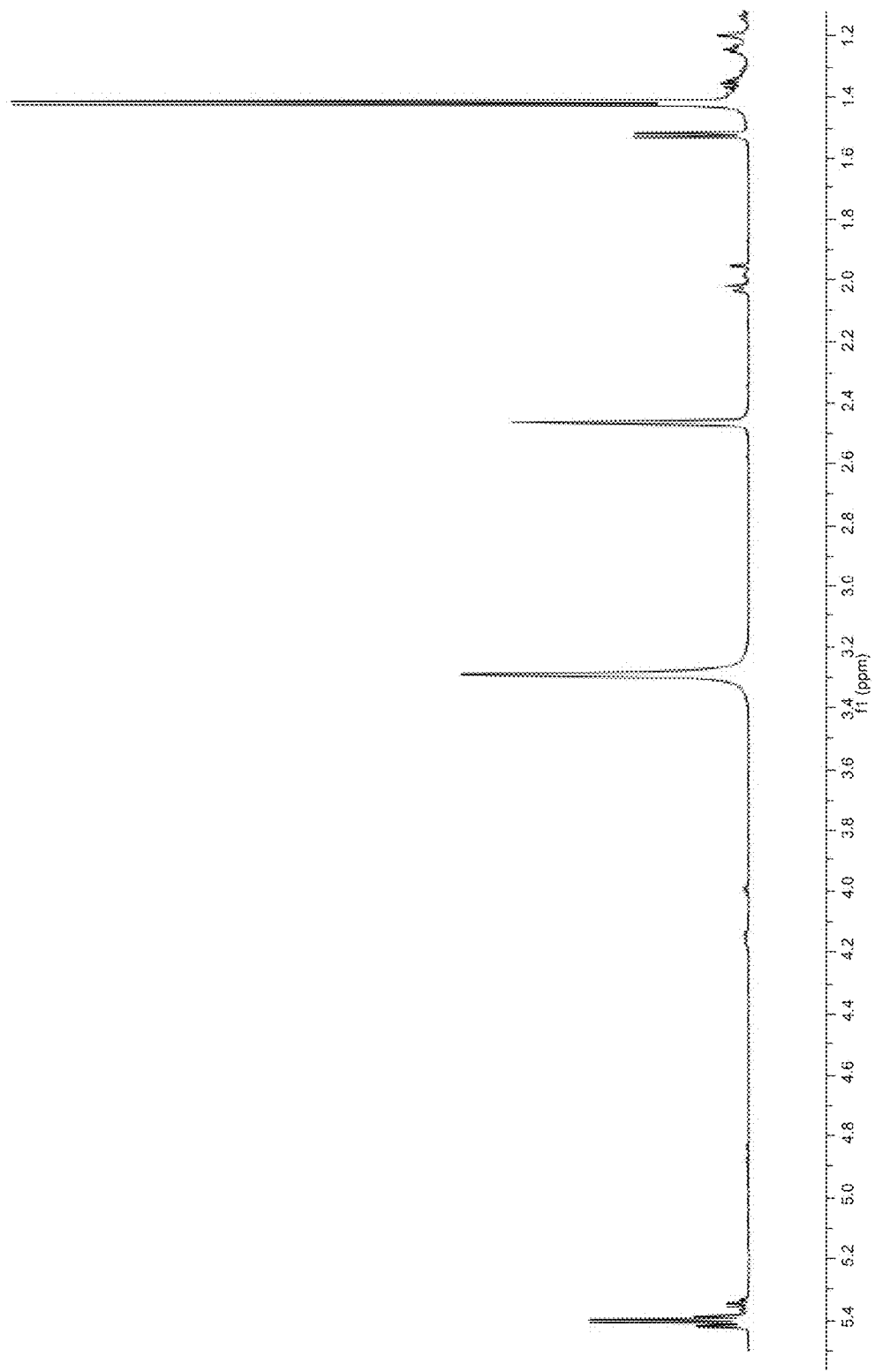
FIG. 11. $^1$H NMR of rac-lactide in DMSO-$d_6$.

In a typical run, 1.0 wt % of SnO (25 mg, 0.186 mmol) is added to the flask containing our synthetic lactic acid oligomers (2.5 g). The flask is equipped with distillation apparatus, and the receiving flask is placed into an oil bath set to 80° C. The reaction flask is placed in a wax bath set to 210° C., and is stirred for 3 hours. During this time, lactide mixture condensed in the receiving flask. This lactide mixture is dissolved in ethyl acetate (3 mL) and washed with 2×3 mL ethyl acetate, then transferred into a 50 mL beaker. The beaker is stored at −15° C. for 72 h. White crystals of rac-lactide recrystallized from the solution is filtrated, dried, weighted and analyzed by $^1$H-NMR (0.69 g, 69% yield). The rac-lactide is >90% pure by $^1$H-NMR (FIG. 11).

Methanol Dehydrogenation

Figure 12:
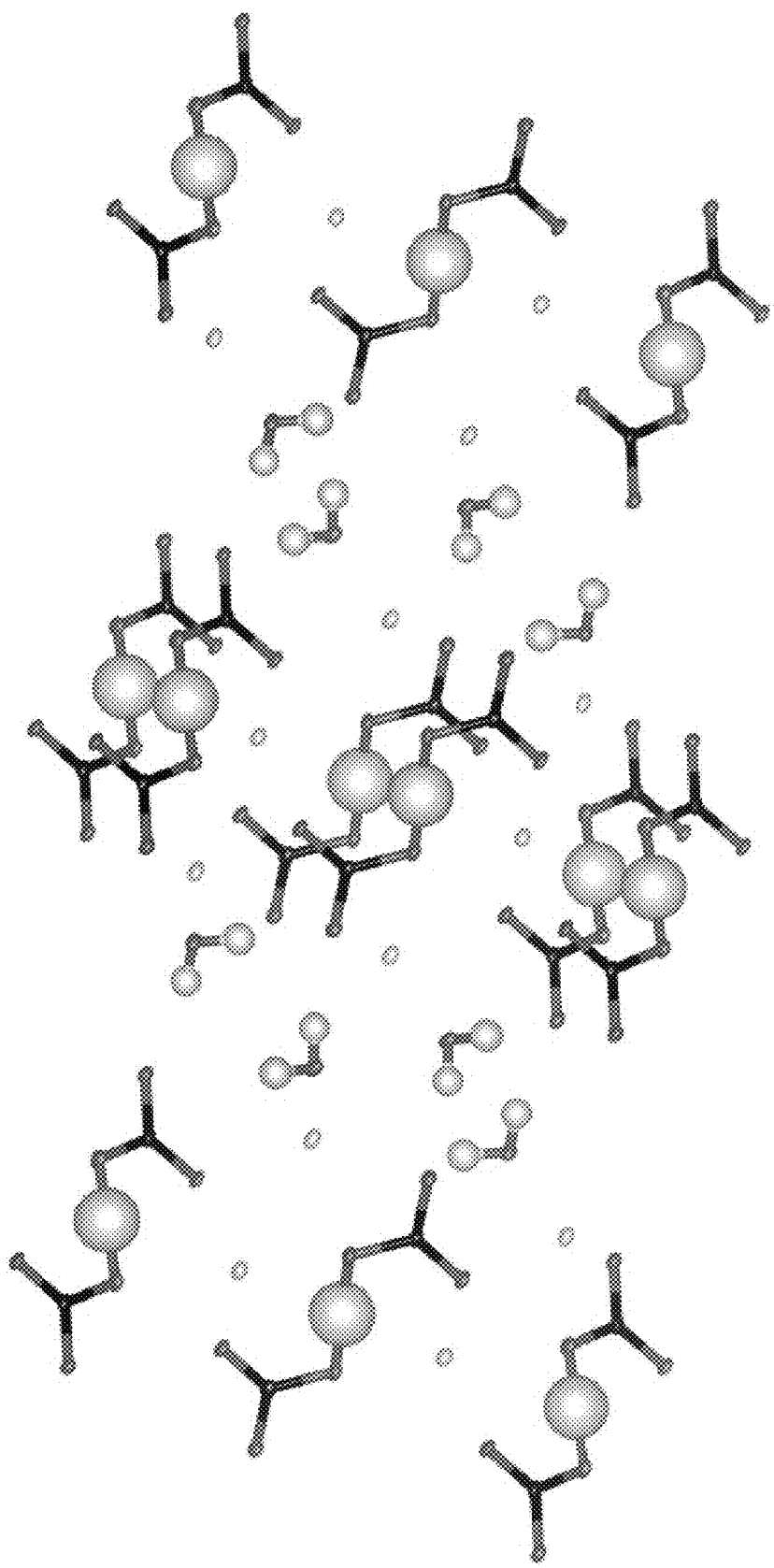
FIG. 12. X-ray structure of $Na_2CO_3 \cdot NaHCO_3 \cdot H_2O$ isolated from methanol dehydrogenation.

In a glovebox, iridium compound 9 (5 mg, 0.008 mmol) and NaOH (2.0 g, 50 mmol) were added to a Schlenk flask equipped with a magnetic stir bar. MeOH (2 mL, 49.3 mmol) and deionized water (6 mL) were also added to the flask outside the glovebox. The flask was then attached to a reflux condenser, which was further connected to water eudiometer. The reaction mixture was refluxed for 12 hours and about 90 mL gas (H$_2$) was collected in the eudiometer. In addition, we crystallized Na$_2$CO$_3$.NaHCO$_3$.H$_2$O from the resulting solution. A TON of 461 (H$_2$) is calculated for this run. An X-ray diffraction structure for the carbonate product follows (FIG. 12).

S7. Mechanistic Study
Catalyst Initiation

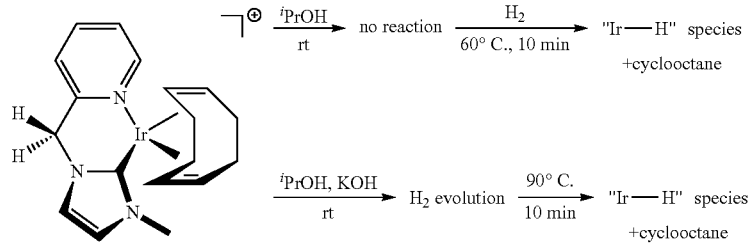

Figure 13:
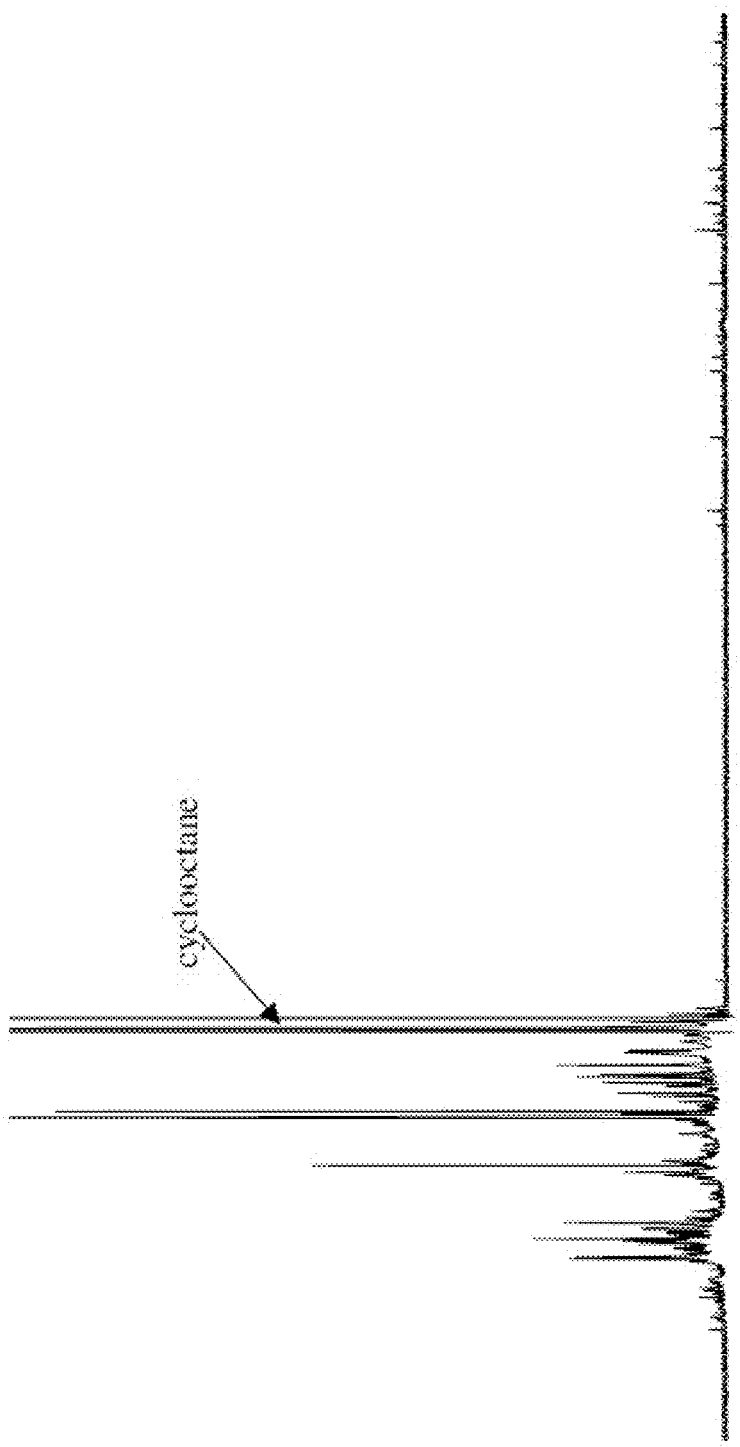
FIG. 13. H$_2$ Evolution at room temperature from dehydrogenation of isopropanol by iridium catalyst 5 in presence of KOH.

In a glovebox, iridium compound 9 (20 mg, 0.032 mmol) and $^i$PrOH (3.7 µL, 1.5 eq) are added to a J. Young tube. 0.6 mL dichloromethane-d$_2$ solvent is added to the same tube. $^1$H NMR shows no reaction at room temperature over 24 hours. The J. Young tube is then gently evacuated, refilled with 1 atm H$_2$, heated to 60° C. for 10 min. $^1$H NMR shows COD fully reduced to cyclooctane. Also a number of Ir—H species formed (FIG. 13).

Figure 14:
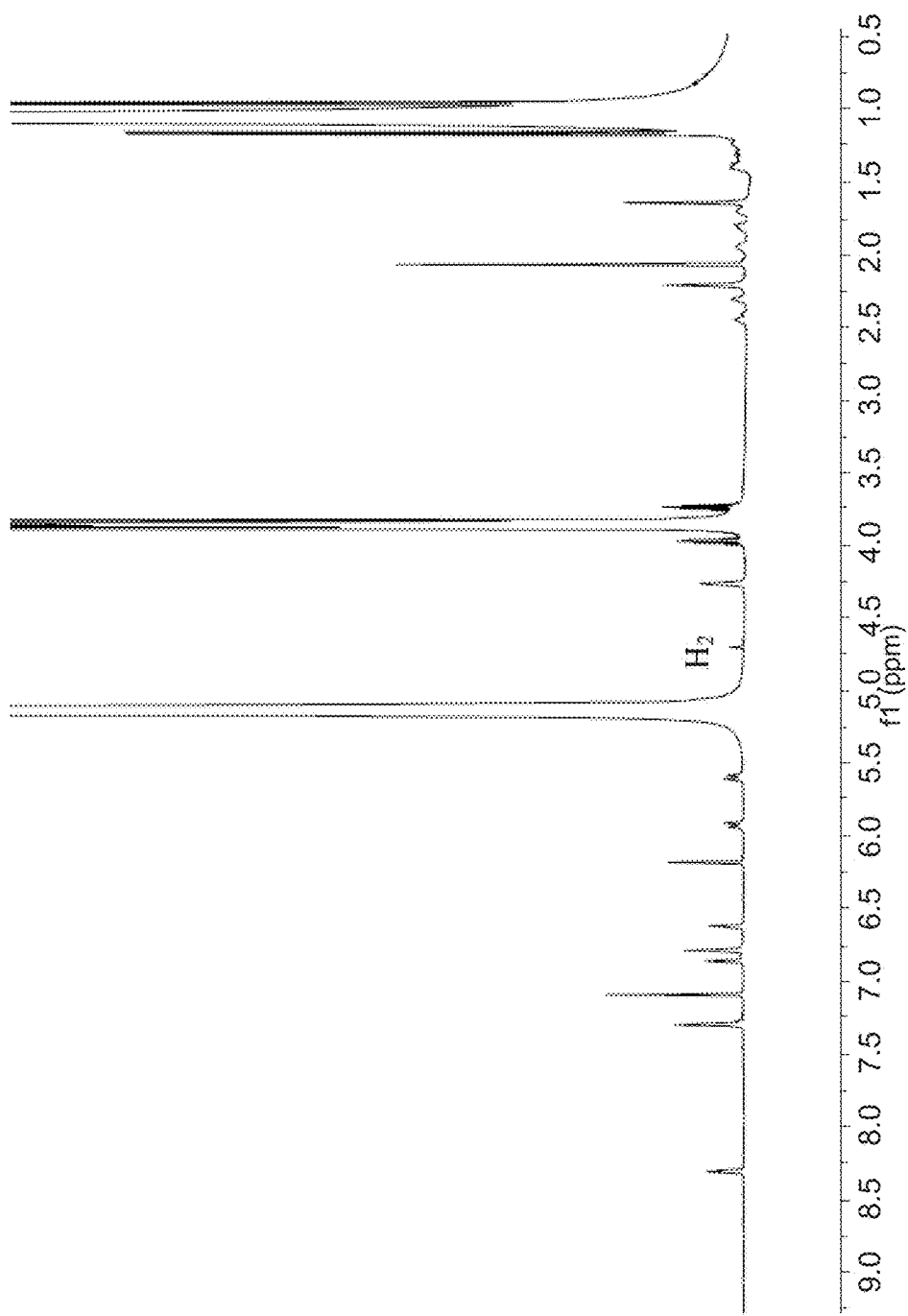
FIG. 14. H$_2$ Evolution at room temperature from dehydrogenation of isopropanol by iridium catalyst 5 in presence of KOH.
Figure 15:
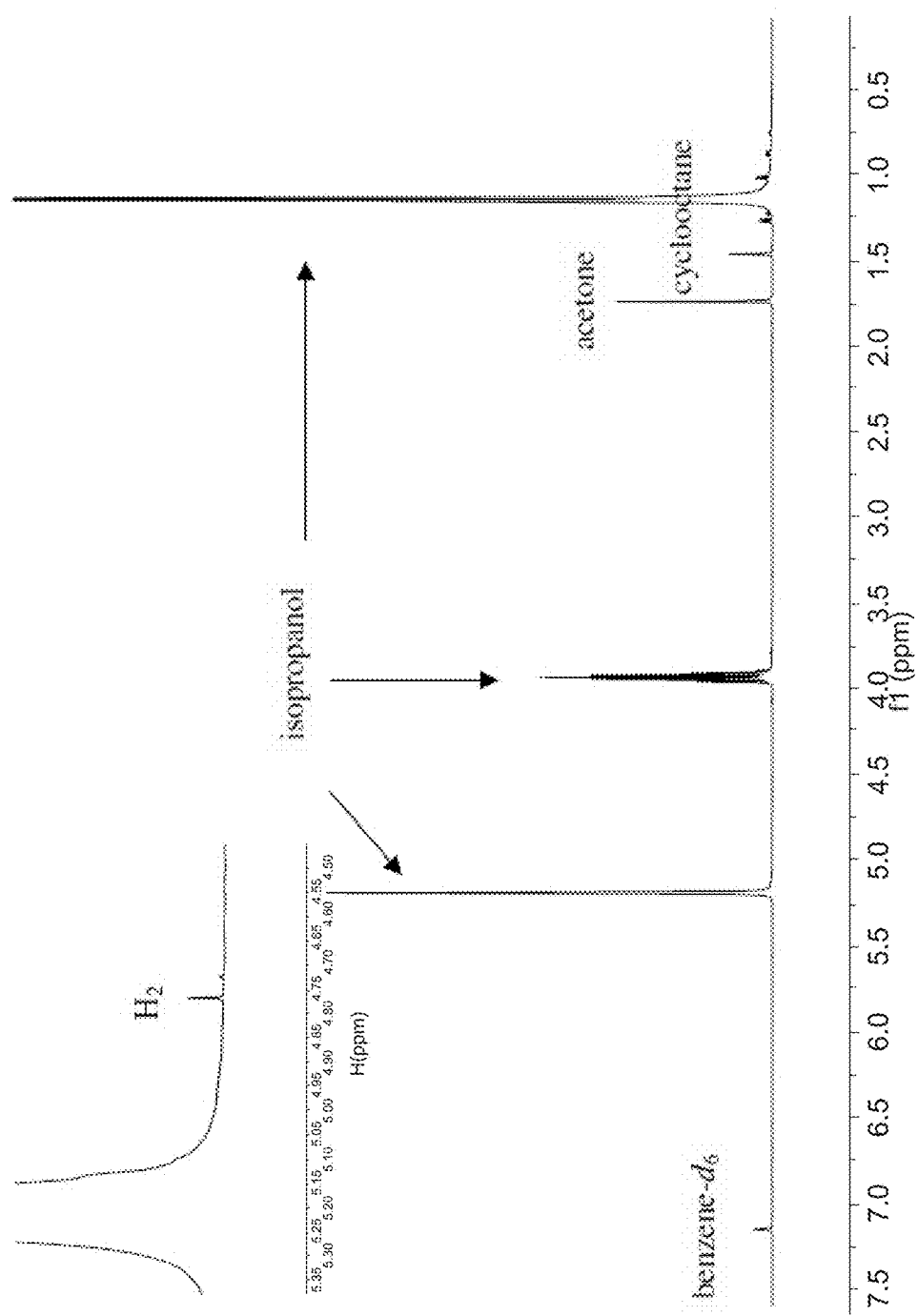
FIG. 15. Formation of cyclooctane from ligand COD in iridium compound 5.

In a glovebox, iridium compound 9 (20 mg, 0.027 mmol) and KOH (15.4 mg, 0.27 mmol) are added to a J. Young tube. 0.6 mL 1:1 isopropanol to benzene-d$_6$ (0.3 mL:0.3 mL) is added to dissolve the solid. $^1$H NMR shows H$_2$ formation at room temperature. The J. Young tube is then closed and heated in an oil bath set to 90° C. for 10 minutes. $^1$H-NMR (FIG. 14) shows full reduction of COD to cyclooctane (FIG. 15).

Probing Catalytic Mechanism
Reversible Ligand Deprotonation in Alcohol Medium

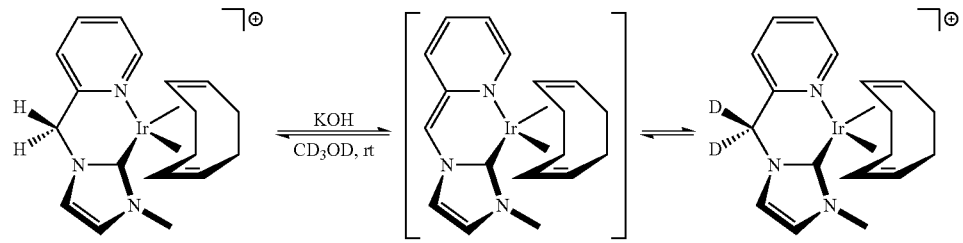

Figure 16:
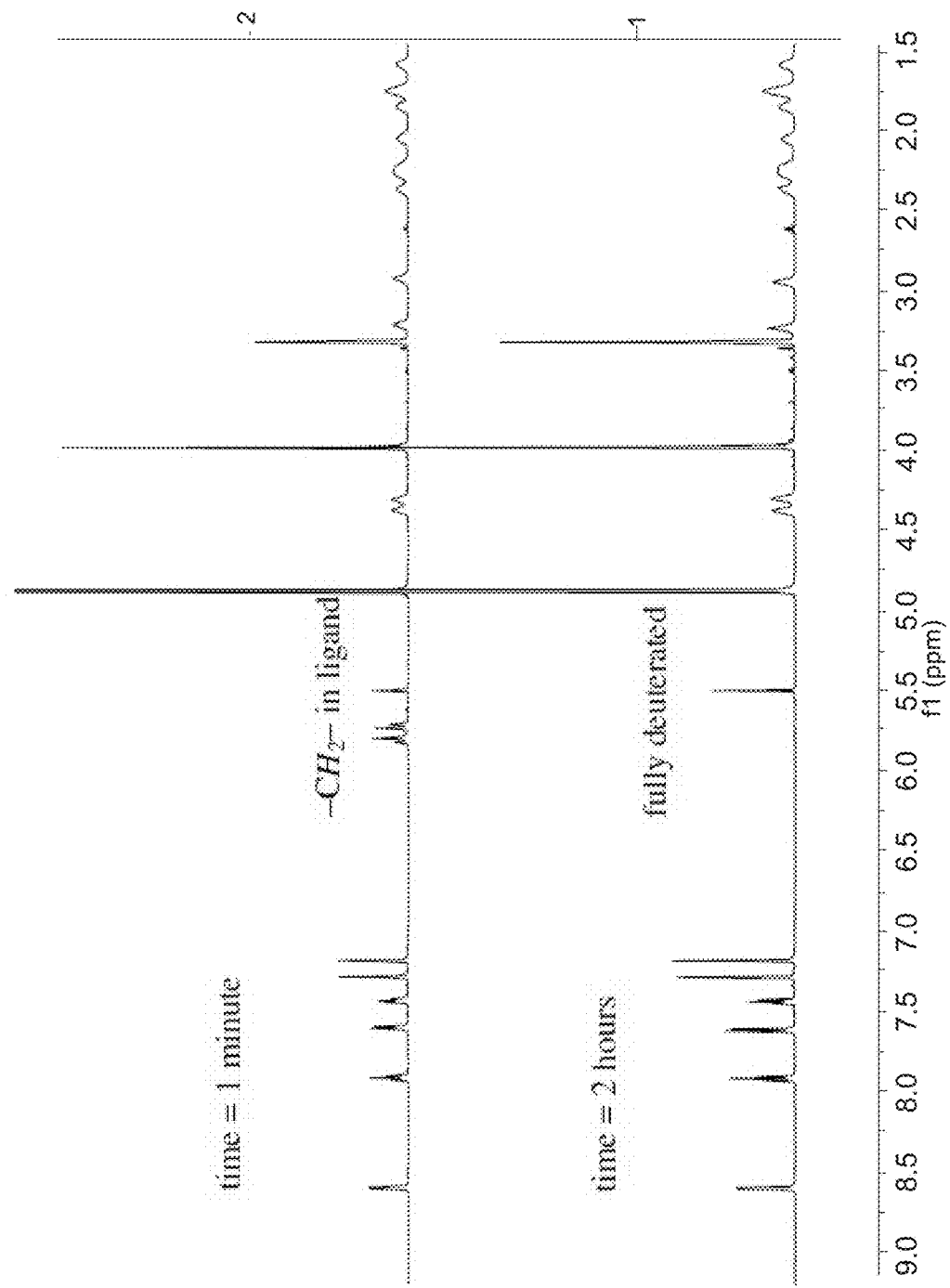
FIG. 16. Room temperature deprotonation at ligand —CH$_2$— to iridium catalyst 9 in CD$_3$OD.

In a glovebox, iridium compound 9 (20 mg, 0.032 mmol) and KOH (1.8 mg, 0.032 mmol) are added to a J. Young tube. 0.6 mL methanol-d$_6$ is added to dissolve the solid. $^1$H NMR shows rapid deuteration at ligand methylene —CH$_2$— group at room temperature (FIG. 16).

COD Displacement

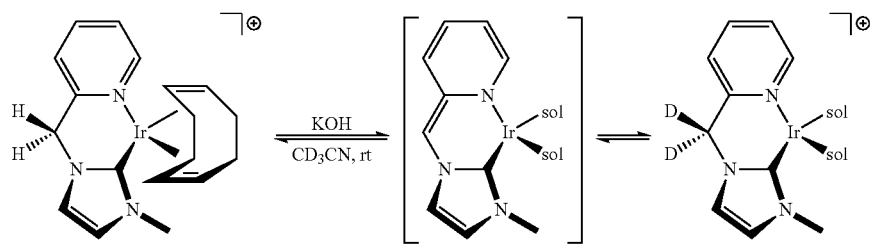

Figure 17:
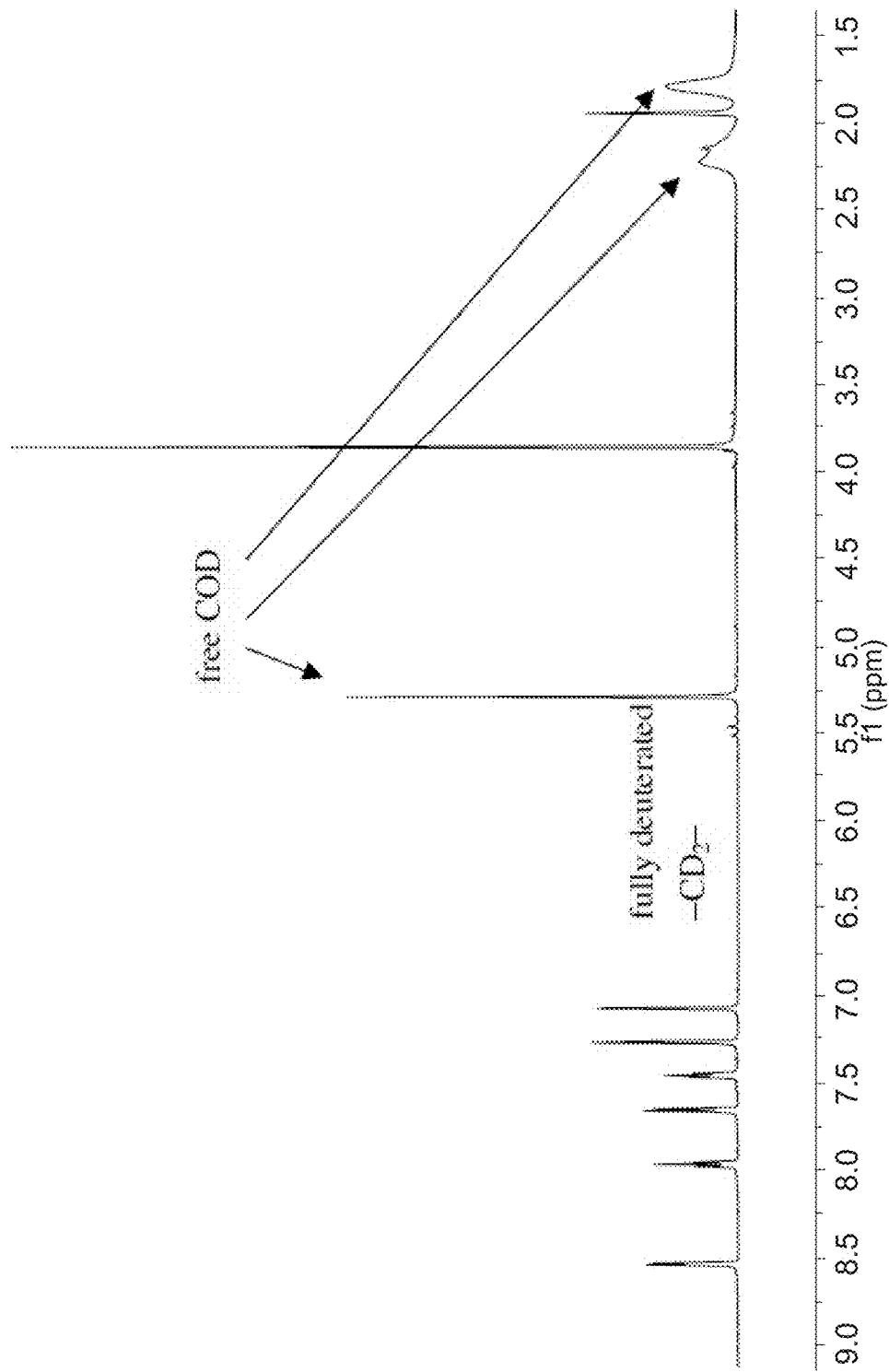
FIG. 17. Room temperature deprotonation at ligand —CH$_2$— to iridium catalyst 9 in CD$_3$CN.

In a glovebox, iridium compound 9 (20 mg, 0.032 mmol) and KOH (1.8 mg, 0.032 mmol) are added to a J. Young tube. 0.6 mL acetonitrile-$d_3$ is added to dissolve the solid. $^1$H NMR shows rapid deuteration at ligand methylene —$CH_2$— group at room temperature within a few minutes (FIG. 17).

Formation of Glyceraldehyde

Figure 18:
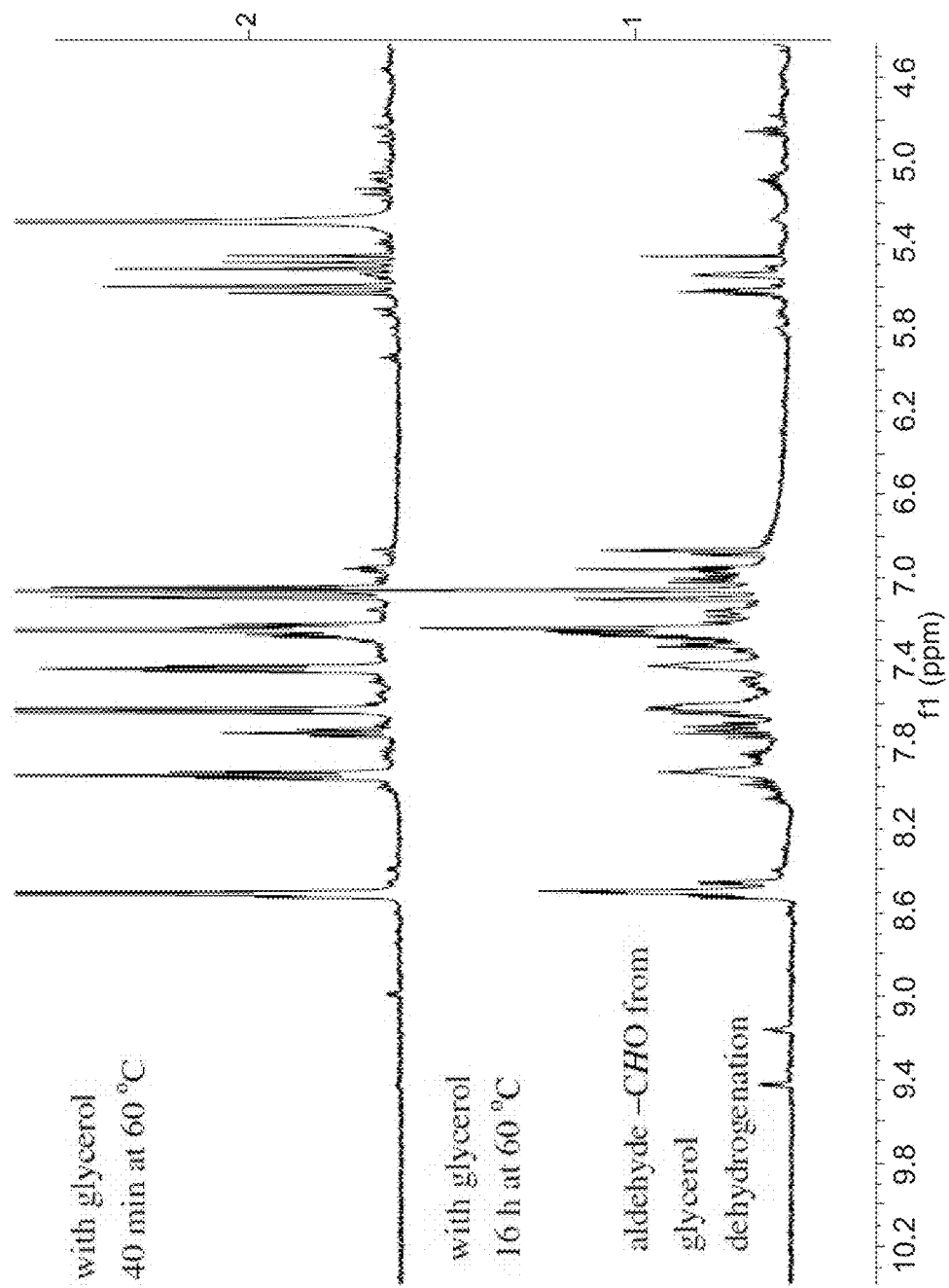
FIG. 18. Glycerol conversion to glyceraldehyde by iridium catalyst 9 in CD$_3$CN.

In a glovebox, iridium compound 9 (20 mg, 0.032 mmol) and KOH (1.8 mg, 0.032 mmol) are added to a J. Young tube. 0.6 mL acetonitrile-$d_3$ is added to dissolve the solid. Then glycerol (10 L, 12.6 mg, 0.136 mmol) is added to the tube and the tube is heated to 60° C. $^1$H NMR (FIG. 18) shows formation of glyceraldehyde as a doublet at 9.4 ppm. This compares well with the experimental DMSO-$d_6$ spectrum, which shows a doublet at 9.61 ppm.[3]

Acidity Comparison Between Ligand in 9 and Glycerol Via Base Titration

In a glovebox, in a dry vial iridium catalyst 9 (1 mg, 0.0016 mmol) is dissolved in 1.0 mL dry THF to give a red solution. In a parallel reaction vial, 9 (1 mg, 0.0016 mmol) and glycerol (1 mg, 0.011 mmol) are also dissolved in 1.0 mL dry THF to give a similar red solution. A stock solution of KO$^t$Bu (10 mg, 0.089 mmol) in 10 mL THF is prepared to titrate the two red THF solutions. In both cases, a color change appeared after 0.9 mL of addition of the KO$^t$Bu solution. In the vial of 9 in THF, the color turned from red to purple; while the vial of 9 and glycerol, the color turned into light yellow. The red colored solution, apparently the deprotonated form of 9, reverts to the yellow color when warmed in the presence of glycerol.

Kinetic Experiments

OH/OD KIE Study

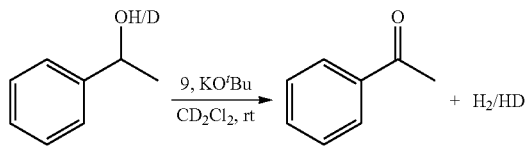

Figure 19:
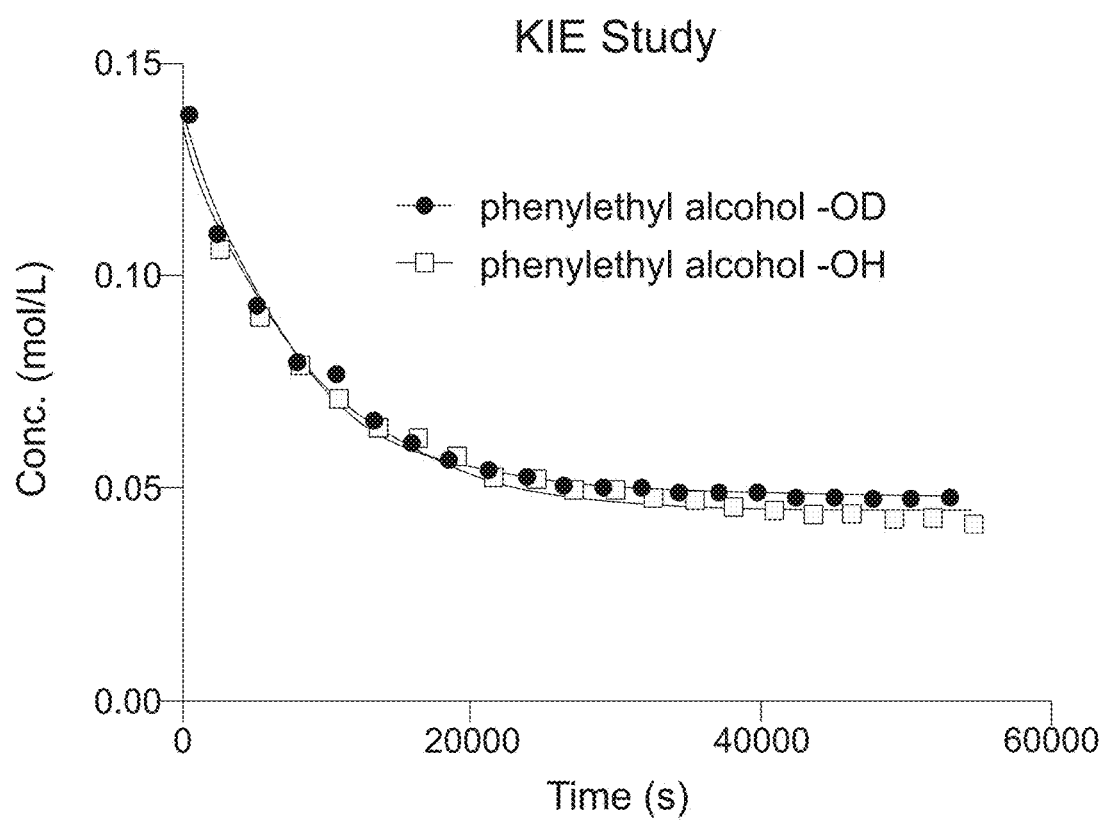
FIG. 19. KIE study of phenylethyl alcohol dehydrogenation by catalyst 9.

In a glovebox, phenylethyl alcohol (OH or OD, 10 μL, 0.083 mmol), iridium catalyst 9 (1 mg, 0.0016 mmol, 2 mol %) and KO$^t$Bu (9.3 mg, 0.083 mmol) are added to a J. Young tube. 0.6 mL dichloromethane-$d_2$ is added to dissolve the solid mixture. The NMR tube is quickly taken to a pre-locked and shimmed NMR instrument for an overnight kinetic study at 25° C. Rate constant of each kinetic run is calculated based on the consumption of the alcohol substrate (FIG. 19). For the —OH experiment, a rate constant of $1.27(5)\times10^{-4}$ s$^{-1}$ could be obtained, while for the —OD run, we observed a rate constant of $1.15(6)\times10^{-4}$ s$^{-1}$. This gives us a KIE$_{OH/OD}$=1.12(11).

Kinetic Dependence on Alcohol Concentration

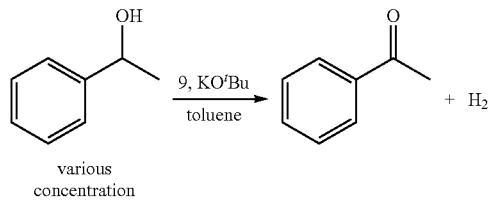

Figure 20:
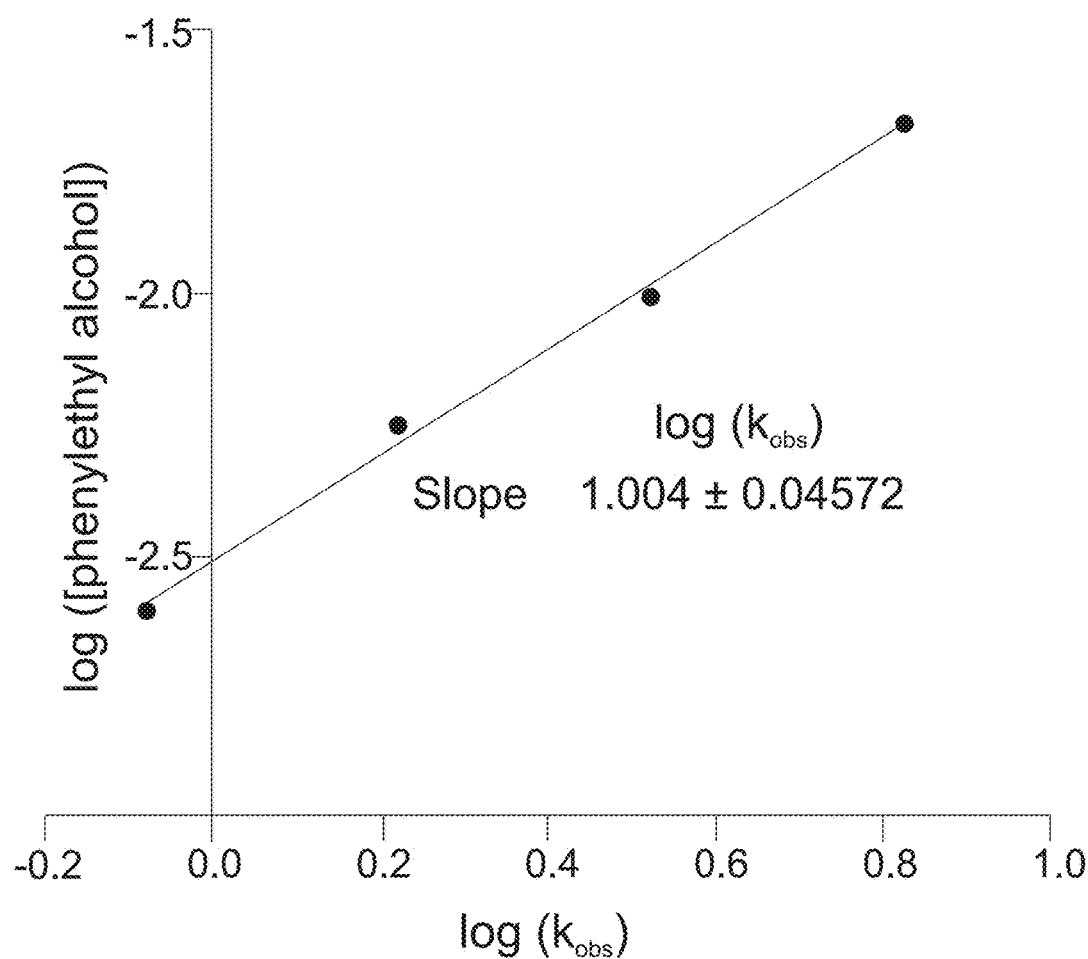
FIG. 20. Kinetic dependence of phenylethyl alcohol.

In a glovebox, phenylethyl alcohol (10 μL, 0.083 mmol, or 20 μL, 0.166 mmol, or 40 μL, 0.332 mmol, or 80 μL, 0.664 mmol), iridium catalyst 9 (1 mg, 0.0016 mmol, 2 mol %) and KO$^t$Bu (0.9 mg, 0.008 mmol) are added to a J. Young tube. 0.6 mL toluene-$d_8$ is added to dissolve the solid mixture. The NMR tube is taken to a pre-heated NMR instrument for a kinetic run at 100° C. Rate constant of each kinetic run is calculated based on the consumption of the alcohol substrate. Rate constants are calculated to be $2.5(5)\times10^{-3}$ s$^{-1}$, $5.8(6)\times10^{-3}$ s$^{-1}$, $9.8(3)\times10^{-3}$ s$^{-1}$, $2.0(2)\times10^{-2}$ s$^{-1}$. A log-log plot (FIG. 20) gives us a slop of 1.004(46), indicating the reaction is first order on the alcohol substrate.

Kinetic Run on (4-Methoxyphenyl)Ethyl Alcohol Dehydrogenation

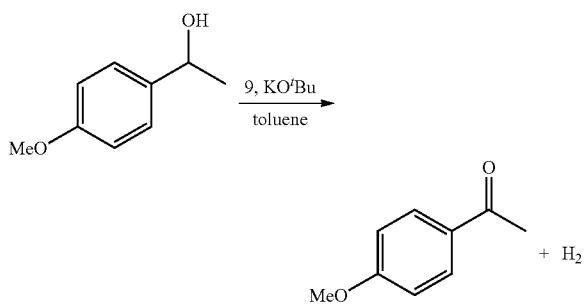

Figure 21:
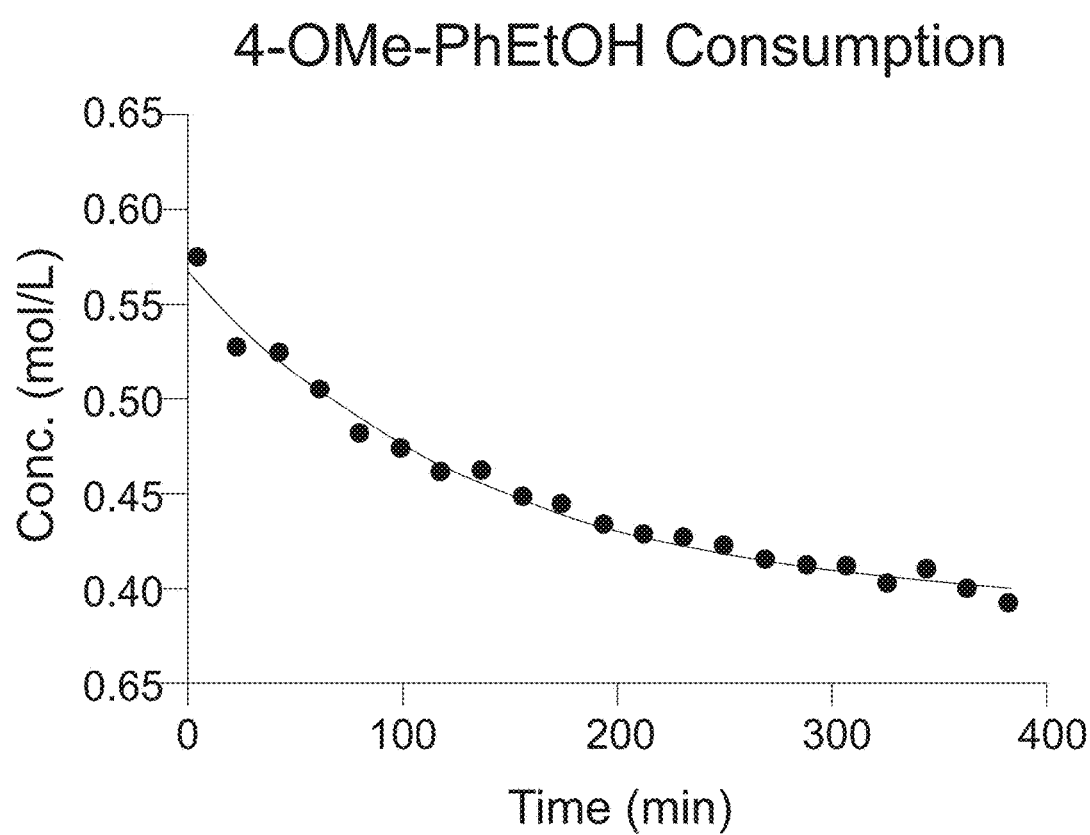
FIG. 21. Kinetic profile of dehydrogenation of 4-methoxy-phenylethyl alcohol.

In a glovebox, (4-methoxyphenyl)ethyl alcohol (12 μL, 0.083 mmol), iridium catalyst 9 (1 mg, 0.0016 mmol, 2 mol %) and KO$^t$Bu (0.9 mg, 0.008 mmol) are added to a J. Young tube. 0.6 mL toluene-$d_8$ is added to dissolve the solid mixture. The NMR tube is taken to a pre-heated NMR instrument for a kinetic run at 100° C. Rate constant of each kinetic run is calculated based on the consumption of the alcohol substrate (FIG. 21). Rate constant is calculated to be $7.3(7)\times10^{-3}$ s$^{-1}$.

Kinetic Runs on Dehydrogenation of $^n$PrOH and $^i$PrOH

Figure 22:
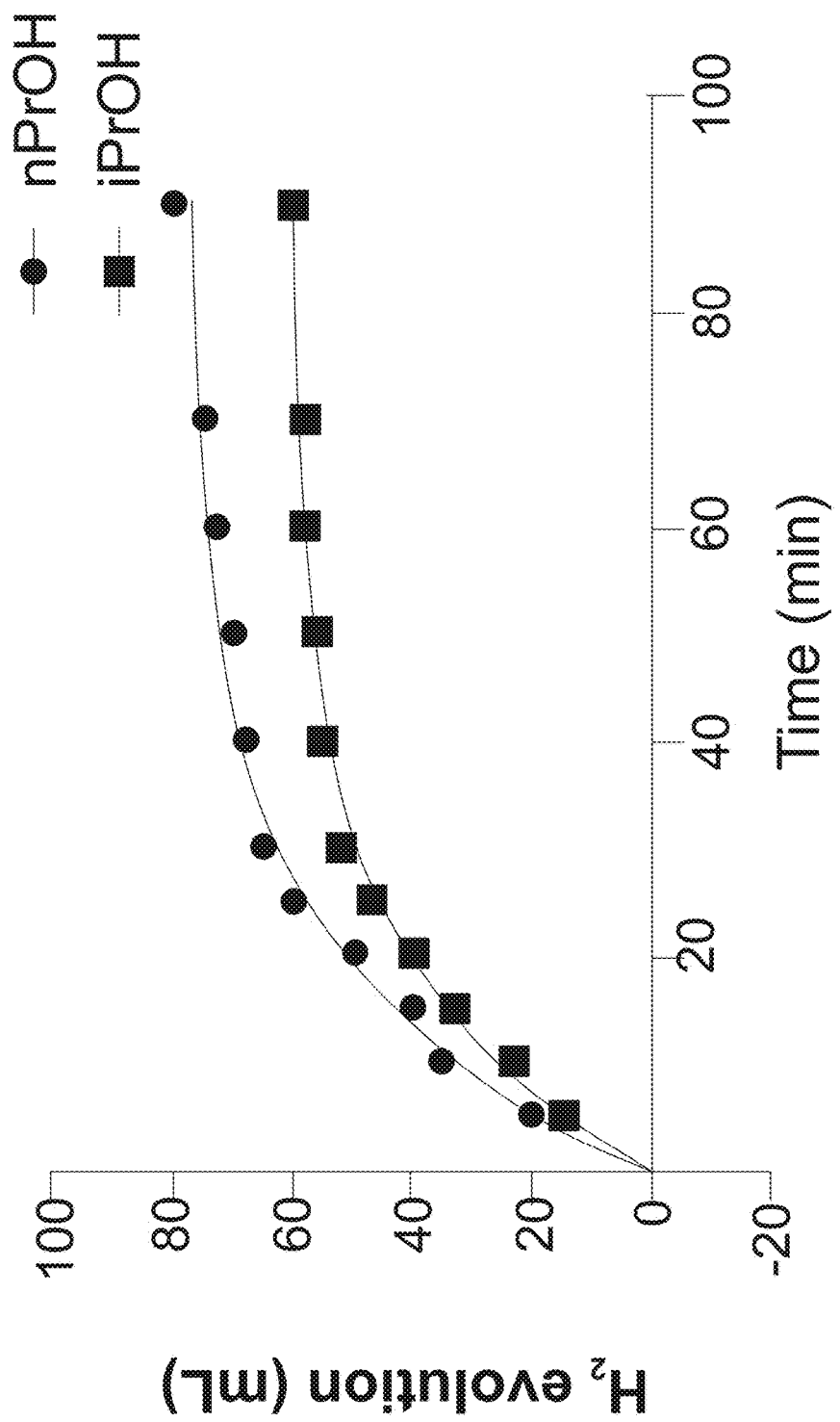
FIG. 22. Kinetic profile on dehydrogenation of 1-propanol and 2-propanol.

In two parallel runs, iridium catalyst 9 (2 mg, 0.0032 mmol) and KOH (367 mg, 6.55 mmol) are dissolved in 2 mL water, 1:1 (v/v) $^n$PrOH:$H_2O$ or $^i$PrOH:$H_2O$. The reaction flasks are placed in oil baths set to 80° C. for 1.5 hours. During this time, $H_2$ evolution is monitored by eudiometry (FIG. 22). The reaction rates are calculated as $5.7(3)\times10^{-2}$ and $5.4(4)\times10^{-2}$, respectively.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

([1]) Anastas, P. T.; Zimmerman, J. B. Innovations in Green Chemistry and Green Engineering, Springer-Verlag New York, 2013.

([2]) U. S. Monthly Biodiesel Production Report 2013-2015: http:/www.eia.gov/biofuels/biodiesel/production/. Accessed 25 Jan. 2016.

([3]) Global Glycerol Market Size, Market Share, Application Analysis, Regional Outlook, Growth, Trends, Competitive Scenario And Forecasts, 2012 to 2020: http:/www.hexaresearch.com/research-report/glycerol-industry/. Accessed 25 Jan. 2016.

([4]) (a) Tan, H. W.; Abdul Aziz, A. R.; Aroua, M. K. Renew. Sustainable Energy Rev. 2013, 27, 118-127. (b) Quispea, C. A. G.; Coronadoc C. J. R.; Carvalho J. A. Jr. Renew. Sustainable Energy Rev. 2013, 27, 475-493.

(⁵) For representative examples see: (a) Pagliaro, M.; Ciriminna, R.; Kimura, H.; Rossi, M.; Pina, C. D. *Angew Chem. Int. Ed.* 2007, 46, 4434-4440. (b) Gu, Y.; Azzouzi, A.; Pouilloux, Y.; Jerome, F.; Barrault, J. *Green Chem.* 2008, 10, 164-167. (c) Katryniok, B.; Kimura, H; Skrzyfiska, E.; Girardon, J.-S.; Fongarland, P.; Capron, M.; Ducoulombier, R.; Mimura, N.; Paul, S. Dumeignil F. *Green Chem.* 2011, 13, 1960-1979. (d). Dam, J.; Hanefeld, U. *ChemSusChem* 2011, 4, 1017-1034; Wang, Z.; Wang, L.; Jiang, Y.; Hunger, M.; Huang, J. *ACS Catal.* 2014, 4, 1144-1147. (e) Haidera, M. H.; Dummer, N. F.; Zhang, D.; Miedziak, P.; Davies, T. E.; Taylor, S. H.; Willock, D. J.; Knight, D. W.; Chadwick, D.; Hutchings, G. J. *J. Catal.* 2012, 286, 206-213. (f) Painter, R. M.; Pearson, D. M.; Waymouth, R. M. *Angew. Chem. Int. Ed.* 2010, 49, 9456-9459. (g) Chung, K.; Banik, S. M.; De Crisci, A. G.; Pearson, D. M.; Blake, T. R.; Olsson, J. V.; Ingram, A. J.; Zare, R. N.; Waymouth, R. M. *J. Am. Chem. Soc.* 2013, 135, 7593-7602. (h) Zhang, Y., Zhang, N., Tangb, Z.-R.; Xu, Y.-J. *Chem. Sci.* 2013, 4, 1820-1824. (i) Villa, A., Veith, G. M. & Prati, L. *Angew Chem. Int. Ed.* 2010, 49, 4499-4502. (j) Brett, G. L.; He, Q.; Hammond, C.; Miedziak, P. J.; Dimitratos, N.; Sankar, M.; Herzing, A. A.; Conte, M.; Lopez-Sanchez, J. A.; Kiely, C. J.; Knight, D. W.; Taylor, S. H.; Hutchings, G. J. *Angew Chem. Int. Ed.* 2011, 50, 10136-10139. (k) Ruiz, V. R.; Velty, A.; Santos, L. L.; Leyva-Pérez, A.; Sabater, M. J.; Iborra, S. Corma, A. *J. Catal.* 2010, 271, 351-357. (l) Lao, D. B.; Owens, A. C. E.; Heinekey, D. M.; Goldberg, K. I. *ACS Catal.* 2013, 3, 2391-2396.

(⁶) U.S. Department of Agriculture, Renewable Chemicals & Materials Opportunity Assessment, Final Report, 2014.

(⁷) (a) Sharninghauseni, L. S.; Camposi, J.; Manasi, M. G.; Crabtree, R. H. *Nat. Commun.* 2014, 5, 5084. (b) Li, Y.; Nielsen, M.; Li, B.; Dixneuf, P. H.; Jungea, H.; Beller, M. *Green Chem,* 2015, 17, 193-198. (c) Sun, Z.; Liu Y.; Chen, J.; Huang, C.; Tu, T. *ACS Catal.* 2015, 5, 6573-6578.

(⁸) CCDC 1415049 (1), 1415050 (2), 1438246 (5) and 1438247 (9) contain supplementary crystallographic data for known (1, 2) and novel (5, 9) Ir compounds.

(⁹) Celaje, J. J. A.; Lu, Z.; Kedzie, E. A.; Terrile, N. J.; Williams, T. J. *Nat. Energy,* in revision. (Attached as revised 11 Jan. 2016.)

(¹⁰) (a) Bayram, E.; Finke, R. G. *ACS Catal.* 2012, 2, 1967-1975. (b) Bayram, E.; Lu, J.; Uzun, A.; Browning, N. D.; Gates, B. C.; Finke, R. G. *ACS Catal.* 2012, 2, 1947-1957.

(¹¹) (a) Montassier, C.; Menezo, J. C.; Renaud, C.; Barbier, J. *J. Mol. Catal.* 1991, 70, 99-110. (b) Maris, E. P.; Davis, R. J. *J. Catal.* 2007, 249, 328-337; Maris, E. P.; Ketchie, W. C.; Murayama, M.; Davis, R. J. *J. Catal.* 2007, 251, 281-294. (c) Roy, D.; Subramaniam, B.; Chaudhari, R. V. *ACS Catal.* 2011, 1, 548-551.

(¹²) (a) Robyt, J. F. Essentials of Carbohydrate Chemistry, Springer-Verlag New York, 1998. (b) Lux, S.; Siebenhofer, M. *Catal. Sci. Technol.* 2013, 3, 1380-1385.

(¹³) Prokopchuk, D. E., Tsui, B. T. H.; Lough, A. J.; Morris, R. H. *Chem. Eur. J.* 2014, 20, 16960-16968.

(¹⁴) (a) Fristrup, P.; Tursky, M.; Madsen, R. *Org. Biomol. Chem.* 2012, 10, 2569-2577. (b) Mueller, J. A.; Goller, C. P.; Sigman, M. S. *J. Am. Chem. Soc.* 2004, 126, 9724-9734.

What is claimed is:

1. An organometallic complex having formula I:

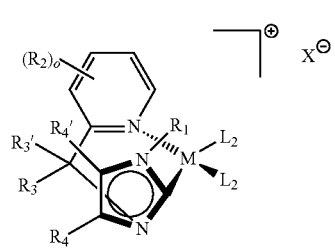

wherein:
M is a transition metal;
o is 0, 1, 2, 3, or 4;
$R_1$ is a $C_{1-6}$ alkyl, a $C_{6-18}$ aryl, or an optionally substituted $C_{5-18}$ heteroaryl;
$R_2$ are independently an optionally substituted $C_{1-6}$ alkyl, halo, $NO_2$, an optionally substituted $C_{6-18}$ aryl, or an optionally substituted $C_{5-18}$ heteroaryl;
$R_3$, $R_3'$ are independently hydrogen, an optionally substituted $C_{1-6}$ alkyl, halo, $NO_2$, an optionally substituted $C_{6-18}$ aryl, or an optionally substituted $C_{5-18}$ heteroaryl;
$R_4$, $R_4'$ are independently hydrogen, an optionally substituted $C_{1-6}$ alkyl, halo, $NO_2$, an optionally substituted $C_{6-18}$ aryl, or an optionally substituted $C_{5-18}$ heteroaryl;
$X^-$ is a negatively charge counter ion; and
$L_1$, $L_2$ are each independently a neutral ligand or $L_1$ and $L_2$ are bonded together to form a bidentate ligand.

2. The organometallic complex of claim 1 wherein M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium.

3. The organometallic complex of claim 1 wherein M is a transition metal selected from the group consisting of ruthenium, rhodium, iridium, and iron.

4. The organometallic complex of claim 1 wherein M is iridium.

5. The organometallic complex of claim 1 wherein $R_1$ is mesityl, methyl, ethyl, butyl, n-propyl, isopropyl, n-butyl, sec-butyl, or t-butyl.

6. The organometallic complex of claim 1 wherein $R_1$ is mesityl or methyl.

7. The organometallic complex of claim 1 wherein $R_2$ are independently an optionally substituted $C_{1-6}$ alkyl, halo, $NO_2$, a $C_{6-18}$ aryl, or $C_{5-18}$ heteroaryl.

8. An organometallic complex having formula III:

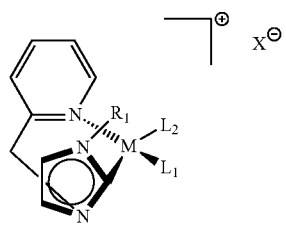

wherein:
M is a transition metal;
$R_1$ is a methyl or mesityl;
$X^-$ is a negatively charge counter ion; and
$L_1$, $L_2$ are each independently a neutral ligand or $L_1$ and $L_2$ are bonded together to form a bidentate ligand.

9. The organometallic complex of claim 8 wherein M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium.

10. The organometallic complex of claim 8 wherein M is a transition metal selected from the group consisting of ruthenium, rhodium, iridium, and iron.

11. The organometallic complex of claim 8 wherein M is iridium.

12. The organometallic complex of claim 8 having formula IV:

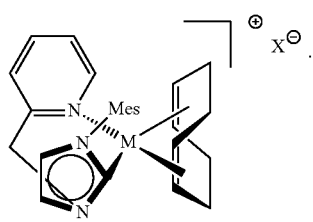

IV

13. The organometallic complex of claim 8 having formula V:

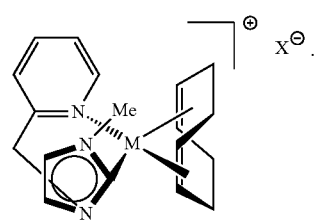

V

14. A method for dehydrogenation a polyol having formula VI:

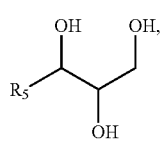

VI the method comprising:
contacting a polyol having formula II with a catalyst system that includes an organometallic complex having formula I to form an oxidized compound having formula VII:

I

VII wherein:
M is a transition metal;
o is 0, 1, 2, 3, or 4;
$R_1$ is a $C_{1-6}$ alkyl, a $C_{6-18}$ aryl, or an optionally substituted $C_{5-18}$ heteroaryl;
$R_2$ are independently an optionally substituted $C_{1-6}$ alkyl, halo, $NO_2$, an optionally substituted $C_{6-18}$ aryl, or an optionally substituted $C_{5-18}$ heteroaryl;
$R_3$, $R_3'$ are independently hydrogen, an optionally substituted $C_{1-6}$ alkyl, halo, $NO_2$, an optionally substituted $C_{6-18}$ aryl, or an optionally substituted $C_{5-18}$ heteroaryl;
$R_4$, $R_4'$ are independently hydrogen, an optionally substituted $C_{1-6}$ alkyl, halo, $NO_2$, an optionally substituted $C_{6-18}$ aryl, or an optionally substituted $C_{5-18}$ heteroaryl;
$R_5$ is a $C_{1-6}$ alkyl or H
$X^-$ is a negatively charge counter ion; and
$L_1$, $L_2$ are each independently a neutral ligand or $L_1$ and $L_2$ are bonded together to form a bidentate ligand.

15. The method of claim 14 wherein the polyol is glycerol and the oxidized compound having formula III is lactic acid.

16. The method of claim 14 wherein the organometallic complex having formula IV OR V:

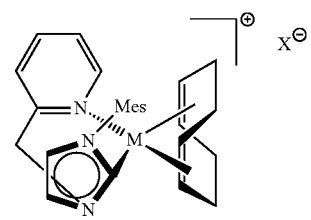

V

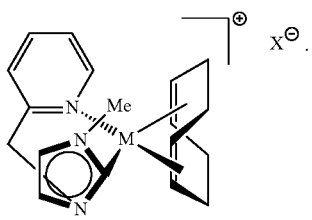

VI

17. A method for dehydrogenation of an alcohol:
contacting an alcohol having formula $R_6OH$ with a catalyst system that includes an organometallic complex having formula I to form an oxidized compound or to liberate hydrogen:

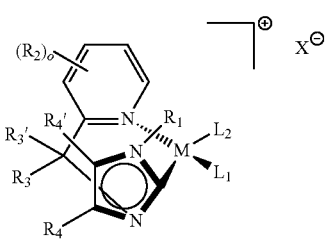

I wherein:
- M is a transition metal;
- o is 0, 1, 2, 3, or 4;
- $R_1$ is a $C_{1-6}$ alkyl, a $C_{6-18}$ aryl, or an optionally substituted $C_{5-18}$ heteroaryl;
- $R_2$ are independently an optionally substituted $C_{1-6}$ alkyl, halo, $NO_2$, an optionally substituted $C_{6-18}$ aryl, or an optionally substituted $C_{5-18}$ heteroaryl;
- $R_3$, $R_3'$ are independently hydrogen, an optionally substituted $C_{1-6}$ alkyl, halo, $NO_2$, an optionally substituted $C_{6-18}$ aryl, or an optionally substituted $C_{5-18}$ heteroaryl;
- $R_4$, $R_4'$ are independently hydrogen, an optionally substituted $C_{1-6}$ alkyl, halo, $NO_2$, an optionally substituted $C_{6-18}$ aryl, or an optionally substituted $C_{5-18}$ heteroaryl;
- $R_6$ is a $C_{1-6}$ alkyl;
- $X^-$ is a negatively charge counter ion; and
- $L_1$, $L_2$ are each independently a neutral ligand or $L_1$ and $L_2$ are bonded together to form a bidentate ligand.

18. The method of claim 17 wherein the alcohol is methanol.

19. The method of claim 17 wherein the organometallic complex having formula IV or V:

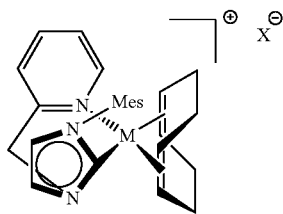

IV

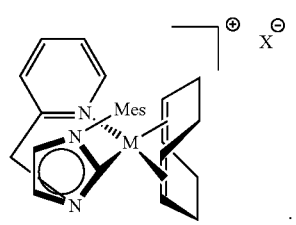

V

* * * * *

UNITED STATES PATENT AND TRADEMARK OFFICE
CERTIFICATE OF CORRECTION

PATENT NO. : 10,202,327 B2
APPLICATION NO. : 15/422728
DATED : February 12, 2019
INVENTOR(S) : Travis J. Williams et al.

Page 1 of 1

It is certified that error appears in the above-identified patent and that said Letters Patent is hereby corrected as shown below:

In the Claims

Column 25, Line 52, Claim 14:
After "A method for dehydrogenation"
Insert: -- of --.

Column 28, Line 22, Claim 19:
In the formula V

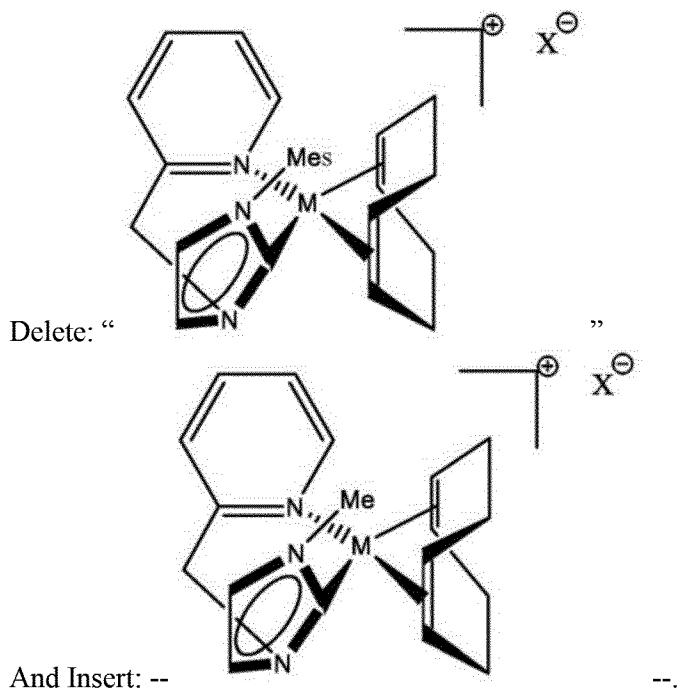

Delete: " "

And Insert: -- --.

Signed and Sealed this
Second Day of July, 2019

Andrei Iancu
*Director of the United States Patent and Trademark Office*